US006951754B2

(12) United States Patent
Hoffmann

(10) Patent No.: US 6,951,754 B2
(45) Date of Patent: Oct. 4, 2005

(54) DNA TRANSFECTION SYSTEM FOR THE GENERATION OF INFECTIOUS INFLUENZA VIRUS

(75) Inventor: Erich Hoffmann, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 26 days.

(21) Appl. No.: 09/844,517

(22) Filed: Apr. 27, 2001

(65) Prior Publication Data

US 2002/0164770 A1 Nov. 7, 2002

Related U.S. Application Data

(60) Provisional application No. 60/200,679, filed on Apr. 28, 2000.

(51) Int. Cl.[7] .............................................. C12N 15/63
(52) U.S. Cl. ................... 435/320.1; 435/69.1; 435/440; 435/456; 435/465; 435/471; 435/475; 435/173.3; 435/235.1; 536/23.1; 536/23.72; 536/24.1
(58) Field of Search ............................. 435/69.1, 440, 435/456, 465, 471, 475, 173.3, 235.1, 320.1; 536/23.1, 23.72, 24.1

(56) References Cited

U.S. PATENT DOCUMENTS 3,992,522 A 11/1976 Chanock et al.

FOREIGN PATENT DOCUMENTS

WO    WO 91/03552 A1    3/1991
WO    WO 00/60050    10/2000

OTHER PUBLICATIONS

Pleschka J Virology 1996 vol. 70, pp. 4188–4192.*
Pekosz Proc. Nat. Acad. Sci, USA Aug. 1999, vol. 96, pp. 8804–8806.*
Neumann 1999 (Aug.) vol. 96, pp. 9345–9350.*
Hoffmann 1997 Generation of an RNA–Polymerase Vector System for the Selective Mutagenesis of Influenza A (in translation).*
Erich Hoffmann et al., "'Ambisense' Approach for the Generation of Influenza A Virus: vRNA and mRNA Synthesis from One Template," Virology, 1999, vol. 267, pp. 310–317.
Erich Hoffmann et al., "Characterization of the Influenza A Virus Gene Pool in Avian Species in Southern China: Was H6N1 a Derivative or a Precursor of H5N1?" J. Virology, 2000, vol. 74, No. 14, pp. 6309–6315.

(Continued)

Primary Examiner—James Housel
Assistant Examiner—Myron G. Hill
(74) Attorney, Agent, or Firm—Darby & Darby

(57) ABSTRACT

The present invention is based on the development of a dual promoter system (preferably a RNA pol I-pol II system) for the efficient intracellular synthesis of viral RNA. The resultant minimal plasmid-based system may be used to synthesize any RNA virus, preferably viruses with a negative single stranded RNA genome. The viral product of the system is produced when the plasmids of the system are introduced into a suitable host cell. One application of the system is production of attenuated, reassortant influenza viruses for use as antigens in vaccines. The reassortant viruses generated by cotransfection of plasmids may comprise genes encoding the surface glycoproteins hemagglutinin and neuramimidase from an influenza virus currently infecting the population and the internal genes from an attenuated influenza virus. An advantageous property of the present invention is its versatility; the system may be quickly and easily adapted to synthesize an attenuated version of any RNA virus. Attenuated or inactivated RNA viruses produced by the present invention may be administered to a patient in need of vaccination by any of several routes including intranasally or intramuscularly.

18 Claims, 13 Drawing Sheets

OTHER PUBLICATIONS

Flick, et al., "*Promoter elements in the influenza vRNA terminal structure,*" RNA, 1996; 2(10):1046–1057.

Luytjes, et al., "*Amplification, Expression, and Packaging of a Foreign Gene by Influenza Virus,*" Cell, 1989; 59(6):1107–1113.

Neumann, et al., "*Genetic Engineering of Influenza and Other Negative–Strand RNA Viruses Containing Segmented Genomes,*" Advances in Virus Research, 1999; 53: 265–300.

Neumann, et al., "*RNA Polymerase I–Mediated Expression of Influenza Viral RNA Molecules,*" Virology, 1994; 202:477–479.

Schnell, et al., "*Infectious rabies viruses from cloned cDNA,*" EMBO Journal, 1994;13(18):4195–4203.

Scholtissek, et al., "*The Nucleoprotein as a Possible Major Factor in Determining Host Specificity of Influenza H3N2 Viruses,*" Virology, 1985; 147:287–294.

Zobel, et al., "*RNA polymerase I catalysed transcription of insert viral cDNA,*" Nucleic Acids Research, 1993; 21(16):3607–3614.

Bergmann, et al., "*The relative amount of an influenza A virus segment present in the viral particle is not affected by a reduction in replication of that segment,*", Journal of General Virology, 1995, 76:3211–3215.

Ghendon, "*Cold–Adapted, Live Influenza Vaccines Developed in Russia,*" Textbook of Influenza, Chapter 29, pp. 391–399.

Nicholson, et al., "*Live Cold–Adapted, Reassortant Influenza Vaccines (USA),*" Textbook of Influenza, Chapter 28, pp. 373–390.

Hoffmann, Erich, Aufbau eines RNA–Polymerase I–Vektorsystems zur gezielten Mutagenese von Influenza A Viren, Giessen 1997 (Doctoral Dissertation).

Hoffman, et al., "*A DNA transfection system for generation of influenza A virus from eight plasmids*", Proc. Nat. Acad. Sci. U.S.A. 2000, vol. 97, pp. 6108–6113.

Hoffman and Webster, "*Unidirectional RNA polymerase 1–polymerase II transcription system for the generation of influenza A virus from eight plasmids,*" J. Gen. Virol. 2000, vol. 81, pp. 2843–2847.

Palese, Peter, et al., "*Negative–strand RNA Viruses: Genetic Engineering and Applications*", Colloquium Paper, Proc. Natl. Acad. Sci., U.S.A., Oct. 1996, vol. 93, pp. 11354–11358.

Neumann, Gabriele, et al., "*Generation of Influenza A Viruses Entirely From Cloned cDNAs*", Microbiology, Proc. Natl. Acad. Sci., U.S.A., Aug. 1999, vol. 96, pp. 9345–9350.

Fodor, Ervin, et al.," *Rescue of Influenza A Virus from Recombinant DNA*", Journal of Virology, American Society for Microbiology, Nov. 1999, vol. 73, No. 11, pp. 9679–9682.

Guan, Yi, et al., "*Molecular Characterization of H9N2 Influenza Viruses: Were They The Donors of the "Internal" Genes of H4N1 Viruses in Hong Kong?*", Microbiology, Proc. Natl. Acad. Sci., U.S.A., Aug. 1999, vol. 96, pp. 9363–9367.

Perez, Daniel R. et al., "*The Matrix 1 Protein of Influenza A Virus Inhibits The Transciptase Activity of a Model Influenza Reporter Genome in Vivo*", Article No. VY989318, Virology, 1998, vol. 249, pp. 52–61.

Xu, Xiyan, et al.," *Genetic Characterization of the Pathogenic Influenza A/Goose/Guangdong/1/96 (H5N1) Virus: Similarly of its Hemagglutinin Gene to Those of H5N1 Viruses form the 1997 Outbreaks in Hong Kong*", Article ID viro. 1999.9820, Virology, 1999, vol. 261, pp. 15–19.

Durbin, Anna P., et al., "*Recovery of Infectious Human Parainfluenza Virus Type 3 from cDNA*", Article No. VY978697, Virology, 1997, vol. 235, pp. 323–332.

Zhou, Yan, et al., "*Membrane–Anchored Incorporation of a Foreign Protein in Recombinant Influenza Virions*", Article No. VY989169, Virology, 1998, vol. 246, pp. 83–94.

Govorkova, E.A., et al., "*African Green Monkey Kidney (Vero) Cells Provide an Alternative Host Cell System for Influenza A and B Viruses*", Journal of Virology, American Society for Microbiology, Aug. 1996, vol. 70, No. 8, pp. 5519–5524.

Pleschka, Stephan, et al., "*A Plasmid–Based Reverse Genetics System for Influenza A Virus*", Journal of Virology, American Society for Microbiology, Jun. 1996, vol. 70, No. 6, pp. 4188–4192.

Muster, Thomas, et al., "*An Influenza A Virus Containing Influenza B Virus 5' and 3' Noncoding Regions on the Neuraminidase Gene is Attenuated in Mice*", Microbilogy, Proc. Natl. Acad. Sci., U.S.A., Jun. 1991, vol. 88, pp. 5177–5181.

Enami, Masayoshi, et al., "*Introduction of Site–specific Mutations into the Genome of Influenza Virus*", Microbiology, Proc. Natl. Acad. Sci., U.S.A., May 1990, vol. 87, pp. 3802–3805.

\* cited by examiner

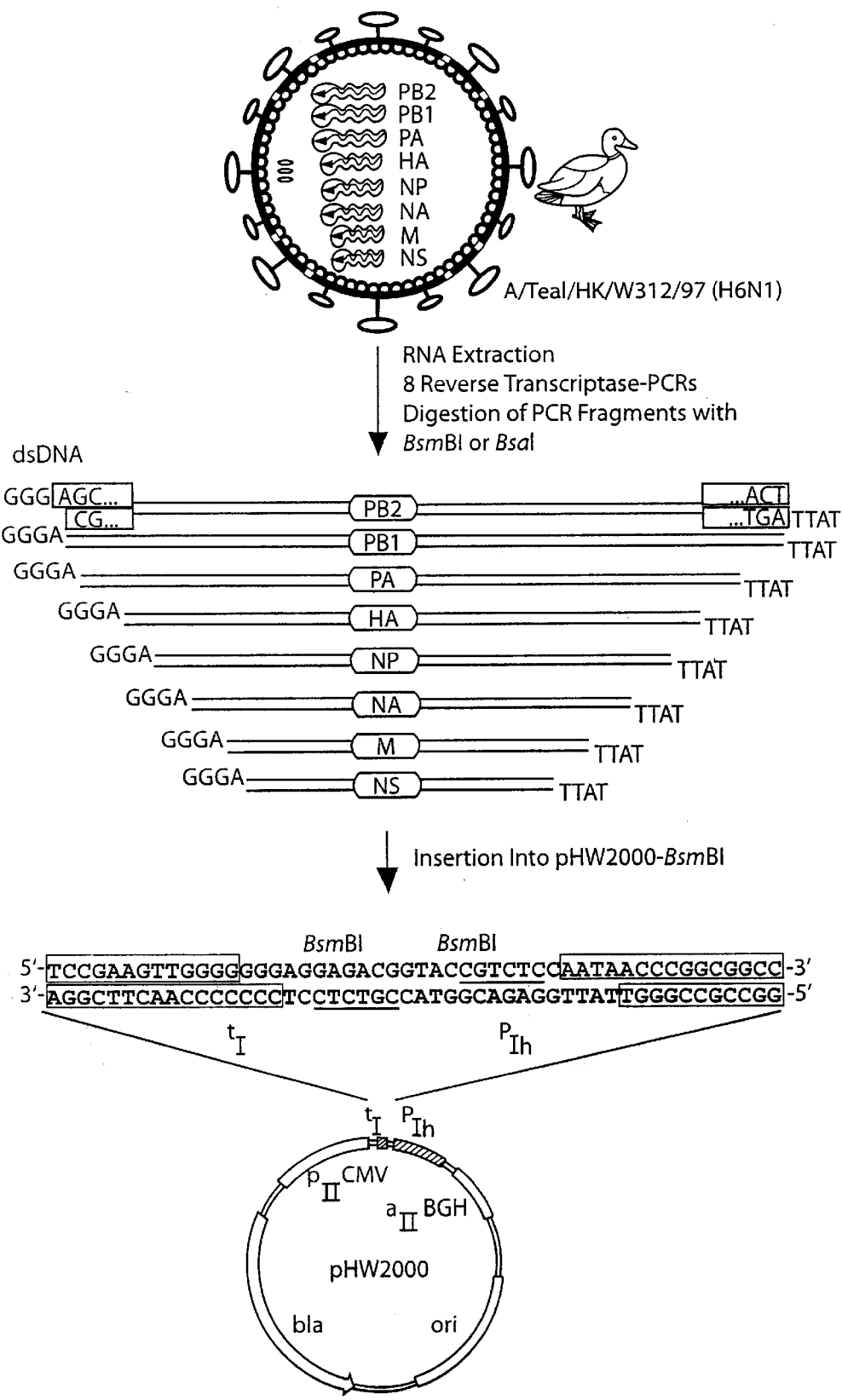

Expression Plasmids

Infectious Influenza A Virus
A/Teal/HK/W312/97 (H6N1)

Unidirectional pol I-pol II Transcription System:

(-) Strand RNA Viruses

Segmented
*Orthomyxoviridae*: Influenza A, Influenza B, Influenza C, Thogoto Virus, Dhori Virus Unimolecular
*Mononegavirales*: Bornaviridae, Filoviridae, Paramyxoviridae, Rhabdoviridae Ambisense RNA Viruses Double - Stranded RNA Viruses (+) Strand RNA Viruses

*Picornaviridae: Enterovirus, Rhinovirus, Cardiovirus, Aphtovirus, Hepatovirus, Parechovirus*

*Flaviviridae: Hepacivirus, Pestivirus*

*Flaviviridae: Flavivirus*

*Togaviridae and Coronaviridae*

DNA TRANSFECTION SYSTEM FOR THE GENERATION OF INFECTIOUS INFLUENZA VIRUS

This application claims the benefit of U.S. Provisional Application No. 60/200,679, filed Apr. 28, 2000 which is herein incorporated by reference in its entirety.

The studies that led to this invention were supported by Public Health Research Grants AI95357, AI29680, AI08831, AI29559 and AI29680 from the National Institute of Allergy and Infectious Diseases. Accordingly, the United States Government may have certain rights in the invention.

FIELD OF THE INVENTION

The present invention relates to the development of a minimum plasmid-based system for the generation of infectious RNA viruses, preferably influenza viruses, from cloned DNA. In particular, this multi-plasmid pol I-pol II system facilitates the generation of both recombinant and reassortment viruses. In preferred embodiments, the invention comprises an eight plasmid pol I-pol II system for generation of influenza viruses. It also has applicability in the recovery of other RNA viruses entirely from cloned cDNA.

BACKGROUND OF THE INVENTION

Life Cycle of RNA Viruses

The genomes of RNA viruses have different configurations, including unimolecular or segmented; single stranded of (+) or (−) polarity or double stranded. However, two essential, common requirements are shared between the viruses: (1) the genomic RNAs must be efficiently copied into a form which can be effectively used for assembly into progeny virus particles and (2) mRNAs which can be efficiently translated into viral proteins must be synthesized. Generally, RNA viruses (except retroviruses) encode and/or carry an RNA-dependent RNA polymerase to catalyze synthesis of new genomic RNA (for assembly into progeny) and mRNAs (for translation into viral proteins). Since eukaryotic host cells typically do not contain machinery for replicating an RNA template or for translating polypeptides from a negative stranded or double stranded RNA template, viruses comprising these nucleic acids in their genomes must carry an RNA polymerase protein in the viral particle. For this reason, deproteinized RNA molecules of negative stranded and double strand RNA viruses (lacking an associated RNA polymerase) are noninfectious. In contrast, deproteinized RNA from the genome of a positive stranded RNA virus is, typically, infectious because encoded viral proteins are translatable by host cellular machinery.

Genomic viral RNA must be packaged into viral particles in order for the virus to be transmitted. Some RNA virus capsids are enveloped by lipid membranes from the infected host cells and others have an outer viral protein shell without a lipid bilayer. Despite these differences between viral capsids, the process by which progeny viral particles are assembled and the protein/protein interactions which occur during assembly are similar. Viral proteins are generally classified as structural and nonstructural proteins. In general, nonstructural proteins are involved in genomic replication, regulation of transcription and packaging. The structural proteins generally perform three types of functions including: (1) binding to genomic RNA (ie, nucleocapsid protein for influenza A virus), (2) bridging between packaged RNA and outer proteins (i.e., matrix protein) and (3) building an outer viral layer (i.e., surface proteins such as hemagglutinin). The assembly into virus particles ensures the effective transmission of the RNA genome from one host cell to another within a single host or among different host organisms.

Influenza Virus

Influenza A virus, an Orthomyxoviridae, is a negative-sense RNA virus with a segmented genome. The genomic RNAs contain one or more open reading frames flanked by noncoding sequences at the 5' and 3' ends (Desselberger et al., Gene 1980, 8: 315). Viral RNAs are associated with viral nucleoprotein (NP) and polymerase proteins (PB1, PB2 and PA) in virions and in infected cells to form ribonucleoprotein (RNP) complexes (Hsu et al., Proc. Natl. Acad. Sci. USA 1987, 84: 8140). Its genetic composition allows this virus to evolve by reassortment of gene segments from different strains; this reassortment creates new variants for which a newly infected organism has no anamnestic immune response. Of the 15 hemagglutinin (HA) and 9 neuramimidase (NA) subtypes of influenza circulating in aquatic birds, three, H1N1, H2N2, and H3N2 subtypes are known to have caused pandemics in humans (Webster et al., Microbiol. Rev. 1992, 56: 152). There is evidence that pigs can serve as an intermediate host ("mixing vessel") for the generation of new strains that are pathogenic in humans (Scholtissek et al., Virology 1985, 147: 287). The H5N1 influenza A outbreak in Hong Kong in 1997 showed that highly pathogenic influenza A viruses can also be transmitted directly from avian species to humans (Claas et al., Lancet 1998, 351: 472; Suarez et al., J. Virol. 1998, 72: 6678; Subbarao et al., Science 1998, 279: 393; Shortridge, Vaccine 1999, 17 (Suppl. 1): S26–S29). The potential of influenza A viruses to generate new pathogenic strains from a vast number of circulating strains in the natural reservoir indicates that disease control requires monitoring these viruses and developing improved antiviral therapies and vaccines. The speed with which new strains develop demands vigilance in this monitoring effort, and stretches the capacity of current technology to produce sufficient quantities of vaccine against a newly identified pathogenic strain to prevent an epidemic or pandemic.

For influenza A virus, reverse-genetics systems have allowed the manipulation of the viral genome (Palese et al., Proc. Natl. Acad. Sci. USA 1996, 93: 11354; Neumann and Kawaoka; Adv. Virus Res. 1999, 53: 265). Unlike positive-strand viruses (i.e., poliovirus), the negative-sense viral RNAs (vRNAs) of influenza A viruses are not infectious. Only vRNA molecules encapsidated with the four viral polymerase complex proteins (PB 1, PB2, PA, NP) are able to initiate a viral replication and transcription cycle. After the ribonucleoproteins (RNPs) penetrate the cell nucleus, the associated proteins begin to transcribe the (−) vRNAs into mRNAs and positive sense complementary RNAs (+) cRNAs. These cRNAs serve as templates for the synthesis of vRNAs. The first reverse-genetics system to be developed for influenza A virus was the RNA-transfection method (Luytjes et al., Cell 1989, 59: 1107; Enami et al., Proc. Natl. Acad. Sci. USA 1990, 87: 3802). After in vitro transcription of virus-like vRNA by the T7 RNA polymerase and reconstitution of viral ribonucleoprotein (vRNA) molecules, genetically altered RNP segments were introduced into eukaryotic cells by transfection. Infection with influenza helper virus resulted in the generation of viruses possessing a gene derived from cloned cDNA. However, the presence of helper virus in RNA and DNA transfection methods severely limits the practical value of these methods since a strong selection system is required to eliminate helper virus.

The establishment of the RNA polymerase I (pol I)-driven synthesis of vRNA molecules in vivo allowed the intracellular production of RNA complexes (Neumann and Hobom, Virology 1994, 202: 477). In this system, virus-like cDNA was inserted between the pol I promoter and terminator sequences (Zobel et al., Nucl. Acids Res. 1993, 21: 3607). Unlike the mRNA transcripts synthesized by RNA polymerase II (pol II), pol I-generated RNAs lack both a 5' cap and a 3' poly (A) tail. Functional vRNP molecules could be generated either by infection with helper virus or by cotransfection of protein expression plasmids encoding PB 1, PB2, PA, or NP (Neumann and Hobom, supra; Flick et al., RNA 1996, 2: 1046; Pleschka et al., J. Virol. 1996, 70: 4188; Zhou et al., Virology 1998, 246: 83).

Recent studies demonstrated that the plasmid-driven expression of all eight vRNAs from a pol I promoter and the coexpression of the polymerase complex proteins result in the formation of infectious influenza A virus (Neumann et al., Proc. Natl. Acad. Sci. USA 1999, 96: 9345; Fodor et al., J. Virol. 1999, 73: 9679). Because the generation of influenza A virus driven entirely from plasmids requires no infection with helper virus, no selection system is needed; therefore, all gene segments can be manipulated without technical limitations. In the system developed by Neumann et al. (supra), the eight cDNAs were inserted between a human pol I promoter sequence (407 bp) and a murine terminator sequence (174 bp). Expression of the four RNP-complex proteins was driven by the human cytomegalovirus promoter. Transfection of 12 plasmids into $10^6$ 293T cells resulted in virus recovery of more than $10^3$ pfu; this efficiency could be increased to $5 \times 10^7$ pfu after the transfection of 17 plasmids. Fodor et al. (supra) developed a system in which the eight cDNAs were inserted between a human pol I promoter sequence (250 bp) and a genomic ribozyme sequence of hepatitis delta virus to ensure the precise 3' end of the vRNA. For the expression of the polymerase complex genes, plasmids containing the adenovirus type 2 major late promoter were used. After transfection of the 12 expression plasmids into Vero cells, only one or two infectious viral particles were rescued from $10^6$ transfected cells.

However, the helper-virus-free system described by Neumann et al. (supra), which contains the pol I and pol II promoters with the influenza virus cDNAs on different plasmids, requires the construction and cotransfection of at least 12 plasmids for virus recovery, and 17 plasmids for efficient virus recovery. Transfection of cells with this many number of plasmids may limit the use of this system to cell lines which have a high transfection efficiency. To be able to rescue virus from different cell types may increase the virus yield by enhancing the replication of influenza A virus in these cells and increase the range of cells suitable for the production of vaccines (Govorkova et al., J. Virol. 1996, 70: 5519).

Thus, there is a need in the art for more efficient generation of recombinant influenza viruses. Moreover, there is a further need in the art for efficient generation of reassortment viruses for vaccine production in response to a newly identified virus strain. The present invention addresses these and other needs in the art by providing systems in which synthesis of both viral genomic negative strand RNA segments (vRNA) and viral mRNA occurs from one template, thereby minimizing the number of plasmids required for virus generation and permitting efficient and predictable reassortment.

Reoviridae Viruses

Viruses from the family Reoviridae, including viruses of the genus Rotavirus, comprise a double stranded, segmented RNA genome. Human rotavirus is the most common viral agent of severe childhood diarrhea in the United States, causing about 50,000 hospitalizations and 20 to 50 deaths per year at an estimated annual cost of more than $1 billion. In developing countries, it is estimated that rotavirus is responsible for one-third of all diarrhea-associated hospitalizations and cause approximately 850,000 deaths annually.

A dual system of reporting rotavirus serotypes exists due to the neutralizing response evoked by two viral proteins (VP), VP7 and VP4. The VP7 serotypes are designated G types, and those derived from VP4 are described as P types. To date, at least 10 G serotypes and at least 7 P serotypes are found in humans. Since VP4 and VP7 genes segregate separately, new rotaviruses are generated by reassortment. In the United States, the serotypes P1 to P4 and G1 to G4 are most frequent; other combinations were reported in countries like India and Egypt. The first licensed human rotavirus vaccine, the rhesus rotavirus vaccine, was formulated to produce serotype-specific protection against the four common serotypes, G1 to G4. However, this vaccine was withdrawn because of an association between vaccination and increased rates of intussusception among vaccine recipients. Thus, there is a need for producing a rotavirus vaccine representing all G and P subtypes which has no unwanted side effects. The current invention provides vectors, (preferably plasmids), methods and host cells which can be employed for generating rotaviruses entirely from cloned cDNA.

Thirteen primary gene products have been defined. To minimize confusion and to facilitate the comparison with proteins with similar functions from other genera of the Reoviridae, the following nomenclature has been employed: according to their migration in SDS-PAGE analysis, starting with the largest protein, the structural proteins have been given the prefix "VP" and nonstructural proteins the prefix "NSP" and the function of each protein is given in brackets. For example, the abbreviation VP1(Pol) indicates that the largest protein in virus particles is the RNA-dependent RNA polymerase. The seven structural proteins assemble into viral particles which comprise three layers of structure: (1) The inner viral core containing the dsRNA genome has three proteins associated with it, two of which (VP1(Pol) and VP3 (Cap)) are directly associated with the genome whereas the third (VP2(T2)) makes up the core shell, (2) the middle protein shell of the virion is made up of 780 VP6(T13) molecules arranged in 260 trimeric units and (3) VP4 and VP7 make up the outer shell. The spike protein VP4 contains a trypsin cleavage site that is important for cleavage into VP5 and VP8, and this cleavage enhances infectivity. Two forms of VP7, derived from different inframe reading frames, VP7(1) and VP7(2), are sought to be incorporated into virions.

Much less is known about the functions of the six nonstructural proteins. Similar to other RNA viruses, it is anticipated that the nonstructural proteins play important roles in virus replication, transcription, translation of viral RNAs and packaging. Indeed, based on the analyses of temperature sensitive viruses in segment 8, it is hypothesized that NSP2(ViP) has a direct role in virus replication. NSP3 is believed to bind to conserved sequences at the 3'-end of viral mRNAs and to the cellular cap binding protein eIF4G thereby specifically upregulating translation of rotavirus mRNAs which have 5'-cap structures but no 3'-polyA-tails. NSP1 appears to be nonessential, but it probably plays an active role in rotavirus replication in cell culture. NSP4 is believed to be involved in virus morphogenesis. The two nonstructural proteins, NSP5 and NSP6, are encoded by two different reading frames from segment 11, but their function in the viral life cycle is not known.

The replication cycle is completed in 10–12 hours at 37° C. Current data suggest that viruses can enter cells through receptor-mediated endocytosis but there may be an alternative mechanism for cell entry. After entering the host cell, the outer virus shell releases the transcriptionally active double-shelled particle into the cytoplasm of the infected cell. Virion-associated enzymes produce 5'-capped, non-polyadenylated mRNAs, which are full-length transcripts from the minus strand of each of the virion genome segments. The viral mRNAs derived from each segment serve two functions: first, they are translated to generate the viral proteins encoded by the segment and second, viral mRNAs are also the templates for genome replication. Genome segment assembly takes place by selection of the different viral mRNAs required to form precore RI. Assembly of the 11 mRNAs is followed by minus strand synthesis, which occurs in 'core-RI' and VP6(T13)-RI, which are present in the 'viroplasms' found in the cytoplasm of infected cell. The next steps in morphogenesis of progeny virions are unique to rotaviruses and involve double-layered particle budding into the endoplasmic reticulum in a process that involves NSP4. This results in the particle transiently acquiring an envelope that is lost during the final maturation steps when the outer virion shell of VP4 and VP7 is added.

A segmented genome, a highly ordered genomic structure and a complex replication cycle present major challenges for the development of a reverse genetic system for generation of rotaviruses. However, the present invention may be used for simple and convenient generation of rotavirus.

Influenza Vaccines

The influenza vaccines currently licensed by public health authorities for use in the United States and Europe are inactivated influenza vaccines. The viruses presenting epidemiologically important influenza A and influenza B strains are grown in embryonated hens' eggs and the virus particles are subsequently purified and inactivated by chemical means. Each year the WHO selects subtypes which most likely will circulate: currently two strains for influenza A (H1N1) and (H3N2), and a B strain.

For the production of a safe and effective vaccine it is important that the selected vaccine strains are closely related to the circulating strains, thereby ensuring that the antibodies in the vaccinated population are able to neutralize the antigenetically similar virus. However, not all viruses found to be closely related are suitable for vaccine production because they grow poorly in eggs. Therefore, it is desirable to attempt to generate a high growth reassortment virus to combine the high virus yield of a laboratory strain (A/PR/8/34) (H1N1) with the antigenic characteristics of the anticipated pathogenic strain. Unfortunately, coinfection with two influenza viruses containing eight segments results in the generation of theoretically $2^8=256$ different progeny viruses. To obtain a high growth virus with the required glycoprotein antigens, a selection method is needed to eliminate the corresponding gene segments from the parental high growth laboratory strain. The selection procedure to obtain the virus with the appropriate glycoproteins and the verification of the gene constellation is a cumbersome and time consuming task. Although the RNP-transfection system (Luytjes et al., Cell 1989, 59: 1107) reduces the possible number of progeny virus, a good selection method is still required.

Live attenuated influenza virus vaccines administered intranasally induce local, mucosal, cell-mediated and humoral immunity. Cold-adapted (ca) reassortment (CR) viruses containing the six internal genes of live, attenuated influenza A/Ann Arbor/6/60 (H2N2) or B/Ann Arbor/1/66, and the haemagglutinin (HA) and neuramimidase (NA) of contemporary wild-type influenza viruses appear to be reliably attenuated. This vaccine appears to be efficacious in children and young adults. However, it may be too attenuated to stimulate an ideal immune response in elderly people, the major group of the 20,000–40,000 individuals in the USA dying each year as a result of influenza infection. Although the sequences of the internal genes of the ca viruses have been reported, the contribution of each segment to the attenuated phenotype is still not well defined. This information can be acquired only by the sequential introduction of specific, defined attenuating mutations into a virus. Although the RNP-transfection method allows the introduction of mutation into the genome of influenza, the need for a selection system and the technical difficulties of reconstituting viral RNPs in vitro limits the use for the manipulation of the internal genes.

Thus, there is a need in the art for development of recombinant influenza vaccines that avoid the use of helper virus, grow well in culture (eggs or cell culture), reliably permit development of reassortment viruses that can be propagated for new vaccine development, and provide for systematic mutation to develop live attenuated virus strains for intranasal vaccination. The present invention addresses these and other needs in the art.

SUMMARY OF THE INVENTION

The present invention advantageously provides an expression plasmid comprising an RNA polymerase I (pol I) promoter and pol I terminator sequences, which are inserted between an RNA polymerase II (pol II) promoter and a polyadenylation signal. The expression plasmid is termed herein a pol I-pol II system, a dual promoter expression system or dual promoter expression plasmid. Such a plasmid optimally contains an RNA virus viral gene segment inserted between the pol I promoter and the termination signal. Preferably, the RNA virus is an influenza virus (e.g., an influenza A or influenza B virus).

The invention comprises two plasmid based systems for generating infectious RNA viruses from cloned genes or cDNA. In one system (bidirectional system), the gene or cDNA is located between an upstream pol II promoter and a downstream pol I promoter. Transcription of the gene or cDNA from the pol II promoter produces capped positive-sense viral mRNA and transcription from the pol I promoter produces negative-sense, uncapped vRNA. In the other system (unidirectional system), the gene or cDNA is located downstream of a pol I and a pol II promoter. The pol II promoter produces capped positive-sense viral mRNA and the pol I promoter produces uncapped positive-sense viral cRNA.

A minimum plasmid-based system of the invention permits generation of infectious RNA viruses from cloned viral cDNA. Such a system comprises a set of plasmids wherein each plasmid comprises one autonomous viral genomic segment of the RNA virus. In each plasmid, the viral cDNA, corresponding to the autonomous viral genomic segment, is inserted between an RNA polymerase I (pol 1) promoter and terminator sequences, thereby resulting in expression of vRNA, which are in turn inserted between a RNA polymerase II (pol II) promoter and a polyadenylation signal, thereby resulting in expression of viral mRNA. Thus, this system employs the bidirectional plasmid technology, and permits efficient reassortment to produce RNA viruses corresponding to the current pathogenic strains in circulation, e.g., in terms of the influenza NA and HA genes, in a background strain well adapted to grow in cell culture or from an attenuated strain, or both. Preferably the virus is an influenza A virus or an influenza B virus.

The invention provides host cells comprising the plasmid-based system for the generation of infectious virions, and methods for producing RNA virus virions, which methods comprise culturing the host cell under conditions that permit production of viral proteins and vRNA.

The plasmid-based system, host cells, and method for producing virions are particularly suited to preparing an RNA virus-specific vaccine. Such methods comprise purifying virions. Purified virions can be inactivated or may be attenuated. Vaccines of the invention can be used for vaccinating against an RNA virus infection. For example, a protective dose of a vaccine comprising inactivated virions can be administered by intramuscular injection. Alternatively, a protective dose of a vaccine comprising attenuated virions can be administered intranasally to a subject.

The invention further provides reassortment virus virions, and vaccine compositions comprising such virions, including inactivated and attenuated virions.

In another advantageous embodiment, the invention provides a method for generating an attenuated RNA virus. This method comprises mutating one or more viral genes in the plasmid-based system, and then determining whether infectious RNA viruses produced by the system are attenuated. Such attenuated viruses can be used to develop intranasal vaccines, including intranasal vaccines with enhanced potency to elicit protective immunity in aged or other populations who are non-responsive to current attenuated vaccines.

DESCRIPTION OF THE DRAWINGS

FIGS. 3A and 3B. Schematic representation of the method developed for the construction and transfection of the eight expression plasmids to recover A/Teal/HK/W312/97 (H6N1). A. Viral RNA was extracted from virus particles. RT-PCR was performed with primers containing segment-specific nucleotides and sequences for the type II restriction endonucleases BsmBI or BsaI. The eight viral PCR fragments were digested with BsmBI or BsaI and inserted into pHW2000 (linearized with BsmBI). This insertion resulted in eight expression constructs where the viral cDNAs are precisely fused to the pol I promoter and terminator (the viral terminal sequences AGC . . . ACT are shown for the PB2 segment in the black rectangles). B. The eight expression plasmids with a pol I promoter and a pol II promoter contain one copy of each of the viral cDNAs of the eight segments. The open reading frames for the 10 viral proteins, are flanked by the segment-specific noncoding regions (gray boxes). Because the used human pol I promoter shows high activity only in cell lines derived from humans or related species, human 293T cells were cocultured together with the standard cell line used for influenza A (MDCK-cells). Viruses produced in the 293T cells after transfection can then infect MDCK cells and replicate.

Figure 1:
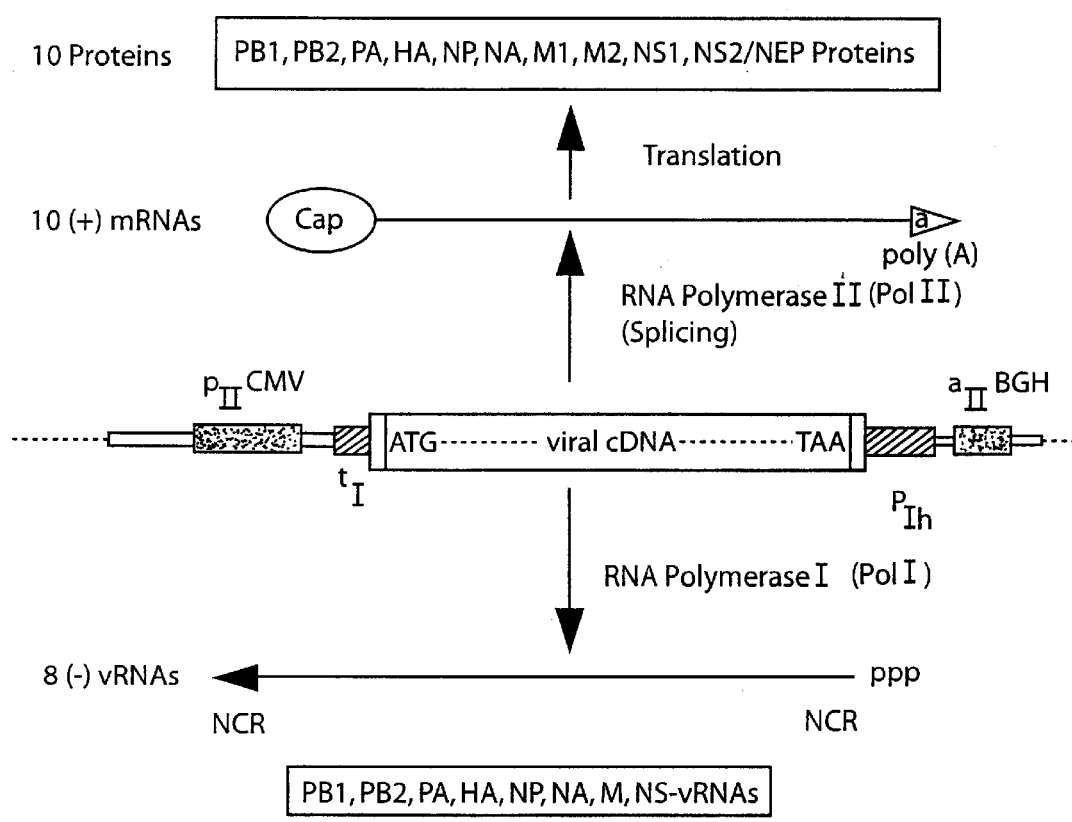
FIG. 1. Schematic representation of the pol I-pol II transcription system for synthesis of vRNA and mRNA. The cDNA of each of the eight influenza virus segments is inserted between the pol I promoter ($P_{Ih}$) and the pol I terminator ($t_I$). This pol I transcription unit is flanked by the pol II promoter ($p_{II}CMV$) of the human cytomegalovirus and the polyadenylation signal ($a_{II}BGH$) of the gene encoding bovine growth hormone. After transfection of the eight expression plasmids, two types of molecules are synthesized. From the human pol I promoter, negative-sense vRNA is synthesized by cellular pot I. The synthesized vRNA contains the noncoding region (NCR) at the 5' and 3' ends. Transcription by pol II yields mRNAs with 5' cap structures and 3' poly A tails; these mRNAs are translated into viral proteins. The ATG of the viral cDNA is the first ATG downstream of the pol II transcription start site.

The present system comprises an outer and an inner transcription unit. The inner transcription unit comprises a promoter (p (+RNA) or p(−RNA)), preferably a pol I promoter. The cDNAs of RNA viruses consist of one or more open reading frames (ORF) which are flanked by non coding regions (NCR). Preferably, there are no sequences intervening between the viral cDNA and the promoter. The lack of intervening sequences is vital because the 5' and 3' ends of genomic vRNA generally contain sequences recognized by viral proteins needed for transcription and replication; additional non-virus sequences typically impedes efficient recognition and replication of the vRNA by viral proteins. The lack of intervening sequences allows the transcribed (−) strand RNA (A) or (+) strand RNA (B) to be used efficiently by viral polymerase proteins. The outer transcription unit has a promoter (p(mRNA)), preferably a pol II promoter which directs transcription of mRNA from the cDNA; the mRNA includes 5' sequences (e.g., methyl G caps) and 3' sequences (e.g., poly A tails) which are required for translational initiation and production of viral proteins. Since the process of translation is tolerant of additional sequences between the promoter, of the outer transcription unit, and the viral cDNA, the presence of intervening sequences from the inner transcription unit do not significantly impede translation of the mRNA.

This system can be modified and improved for RNA viruses other than influenza virus by using different promoters in the inner transcription unit (e.g., pol II, pol III, T3, SP6, T7 or any other promoter for a DNA-dependent RNA polymerase) and termination elements or ribozymes for the intracellular synthesis of viral RNA with exact 5' and 3' ends (discussed infra). Hammerhead ribozymes or hepatitis delta virus (HDV) ribozyme can be employed for generatiion of viral RNA with exact ends (Schnell et al., EMBO J. 1994, 13: 4195; Pleschka et al., J. Virol. 1996, 70: 4188; Herold, J. et al., J. Virol 2000, 74 (14): 6394–400).

The outer transcription unit may comprise a pol I or III promoter, a T7 RNA polymerase promoter, a T3 RNA polymerase promoter, SP6 RNA polymerase promoter, or any other promoter for a DNA-dependent RNA polymerase. If the promoter in the outer transcription unit directs synthesis of a transcript which lacks a methyl G cap, an Internal Ribosome Entry Site (IRES) may be placed at the 5' end of the cDNA coding sequence to facilitate translational initiation (discussed infra).

It is noteworthy that the vector pHW2000 has a T7 promoter between the CMV-promoter and the termination site. Pol II transcripts are synthesized in the nucleus, whereas T7-transcripts are synthesized in the cytoplasm of cells expressing T7 RNA polymerase. Hence, transcripts originating from more than one promoter of an outer transcription unit can be produced resulting in different mRNAs. Thus, expression plasmids derived from pHW2000 allow the rapid evaluation of whether the pol II or T7 promoter or the combination of both is optimal for mRNA synthesis of positive strand viruses which have an Internal Ribosome Entry Site (IRES).

Figure 8:
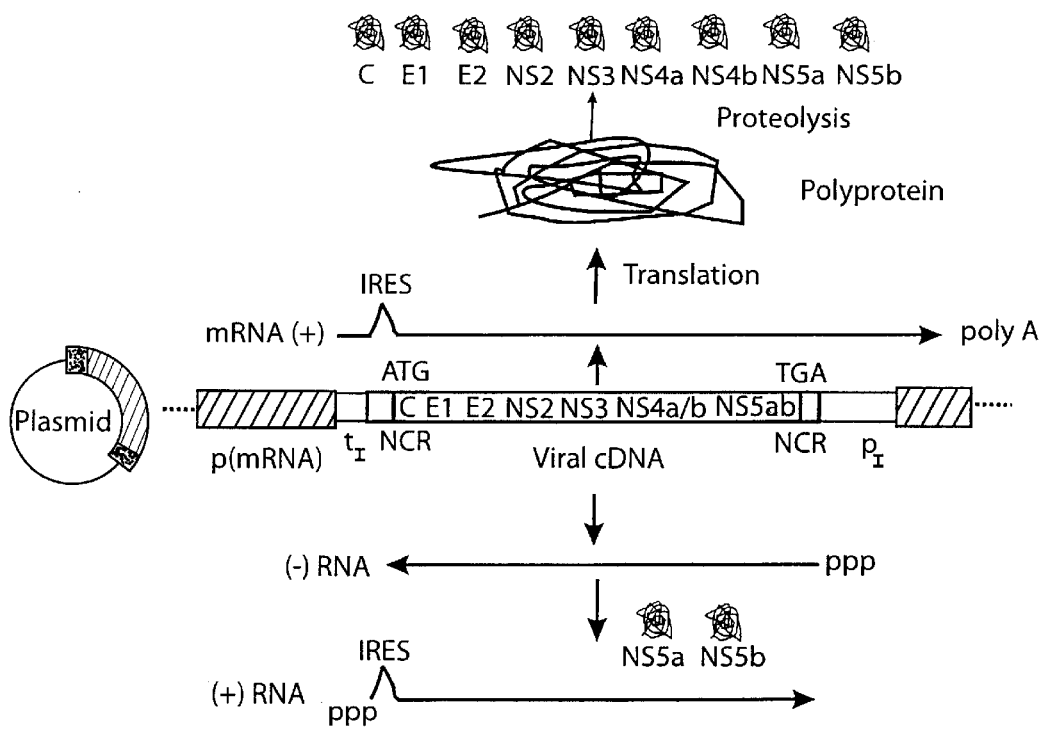

FIG. 8. Dual promoter system for the generation of a (+) strand RNA viruses. The present invention may also be adapted to produce viruses comprising a positive strand, unimolecular genome, such as hepatitis C virus. In this embodiment, a cDNA comprising the hepatitis C virus genome (approximately 9500 nucleotides) is inserted in a construct that allows efficient transcription of the cDNA intracellularly into mRNA and a full length negative RNA (bidirectional approach) or mRNA and full length positive RNA (unidirectional approach). The cDNA consists of one open reading frame (ORF) which is flanked by the non-coding regions (NCR). In the figure, an expression plasmid containing the bidirectional system is shown. The full length cDNA is inserted between a pol I (pI) promoter and termination sequences (tI) resulting in full length (−) strand RNA synthesis after transfection.

The inner transcription unit is flanked by an outer transcription unit which has a promoter (p(mRNA)) to drive mRNA synthesis. Preferably, this promoter is a pol II promoter. However, if the synthesized RNA has an internal ribosomal entry site (IRES), the pol II promoter may be substituted by a pol I, pol III, SP6, T7 or T3 promoter (use of T3 or T7 promoters requires that the T3 or T7 polymerase proteins be expressed either by cotransfection of a plasmid encoding the polymerases or use of a stable cell line expressing the polymerases). At the 3'-end of the outer transcription unit, either a poly A signal or an inserted poly A sequence is used to provide a polyA tail for the synthesized mRNA.

The resultant mRNA is translated into a large polyprotein precursor that is cleaved co- and posttranslationally to yield individual structural and nonstructural viral proteins.

The nonstructural proteins NS5a and NS5b, which are the RNA-dependent RNA polymerase proteins use the (−) RNA synthesized by the inner transcription unit as a template to initiate the viral replication/transcription cycle. Thus, (+) RNA/mRNA is produced which is used for translation into protein. Ultimately infectious viruses are generated which contain (+) RNA together with viral structural proteins.

Figure 9:
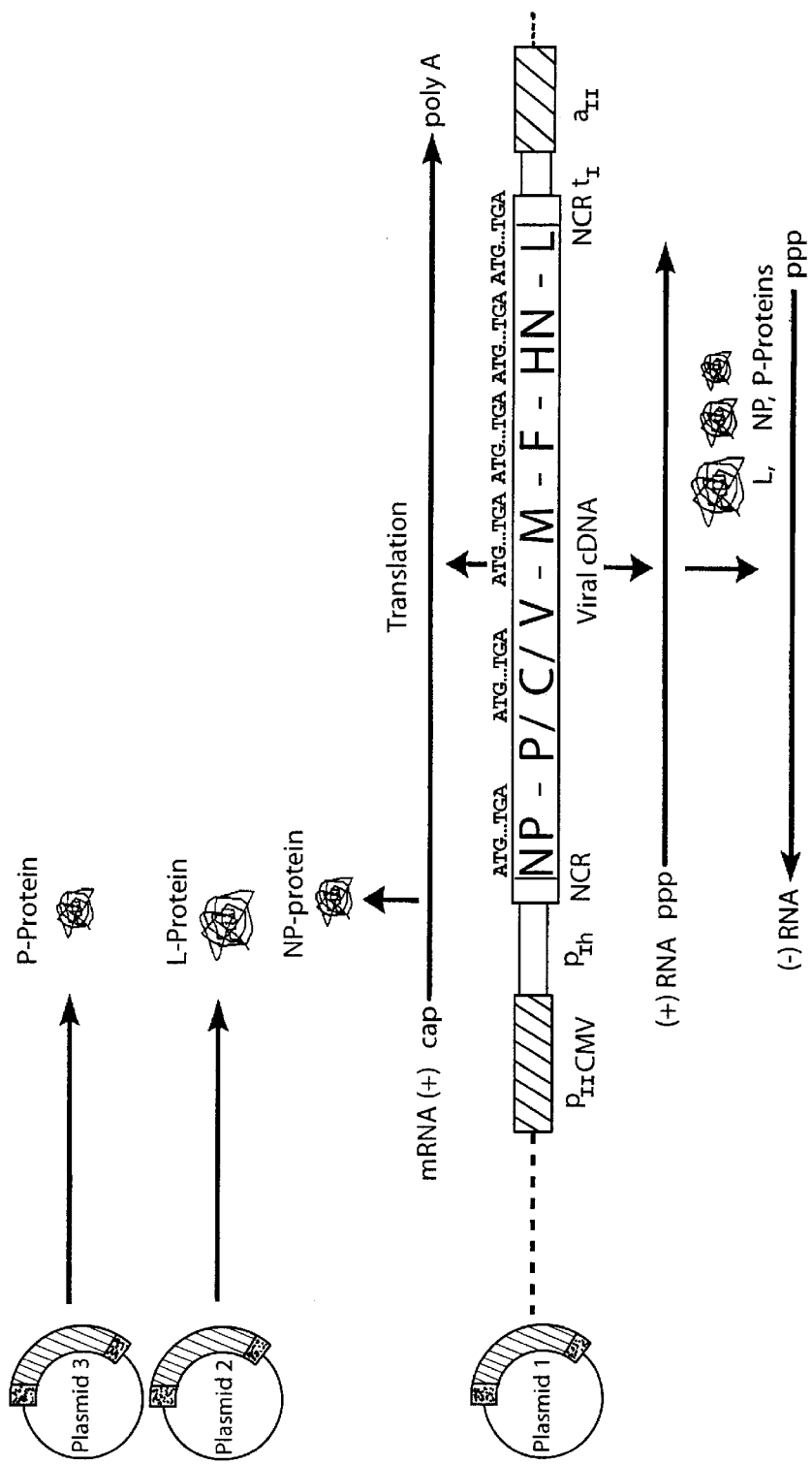
Figure 10:
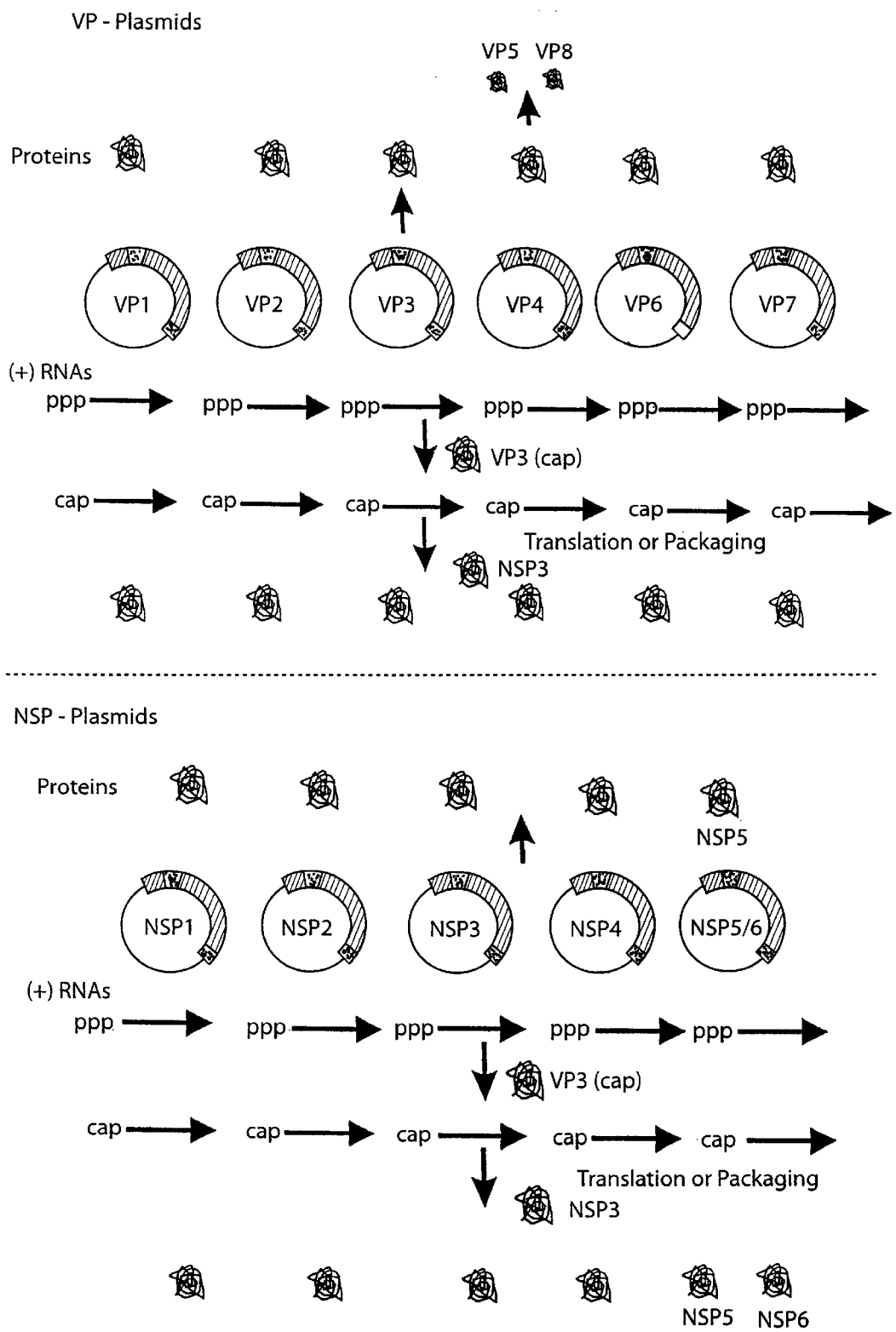
Figure 11A:
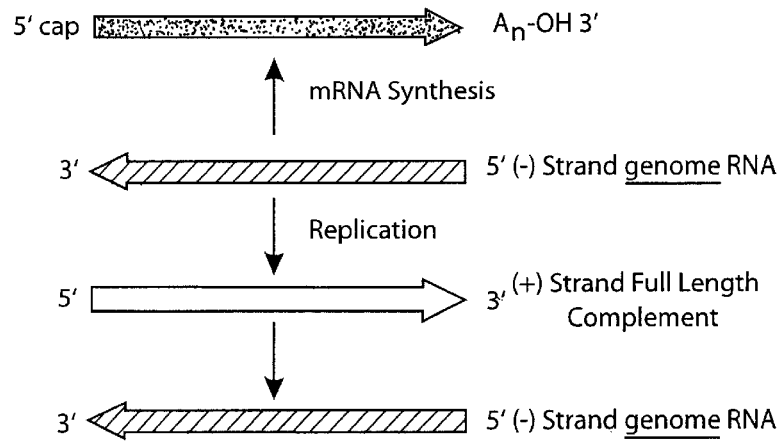
Figure 11A:
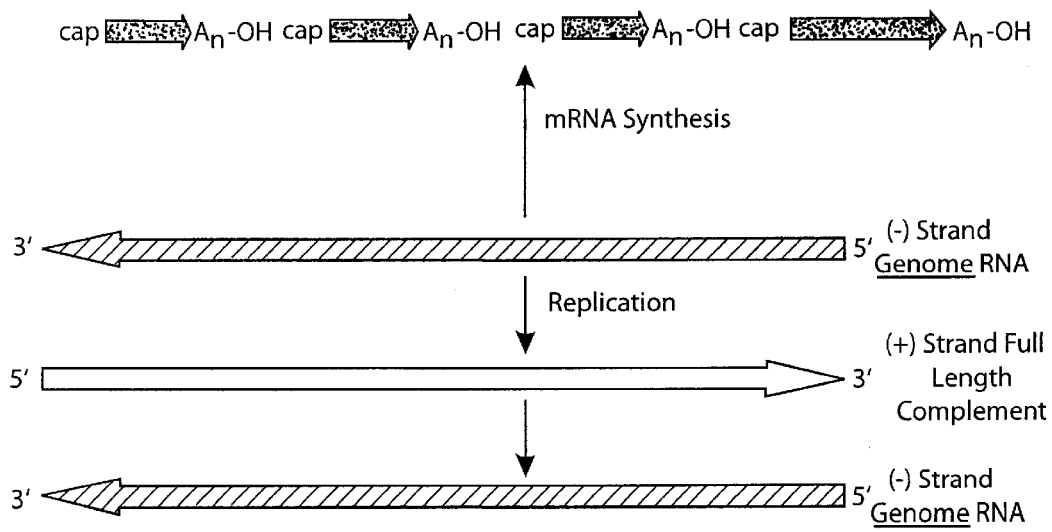
Figure 11B:
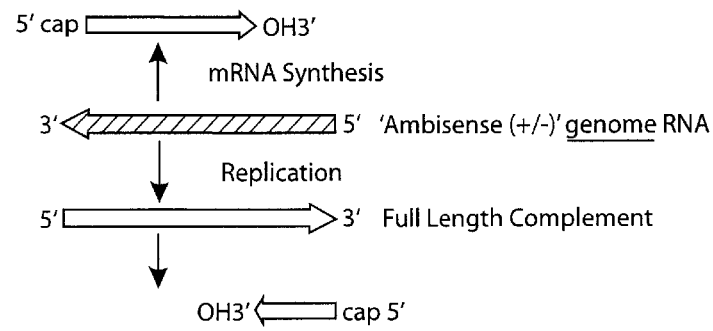
Figure 11C:
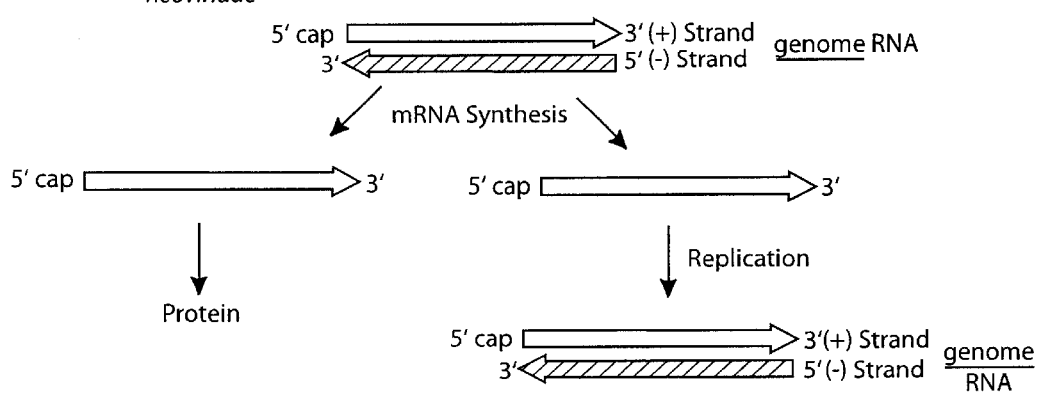
Figure 11D:
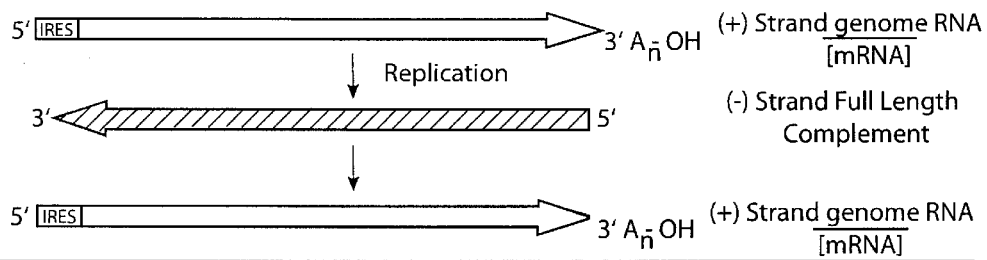
Figure 11D:
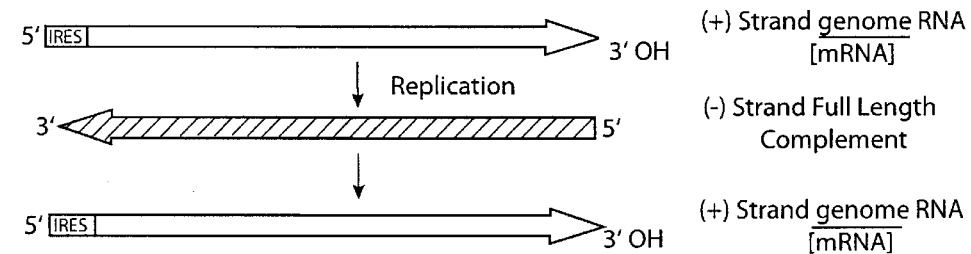
Figure 11D:
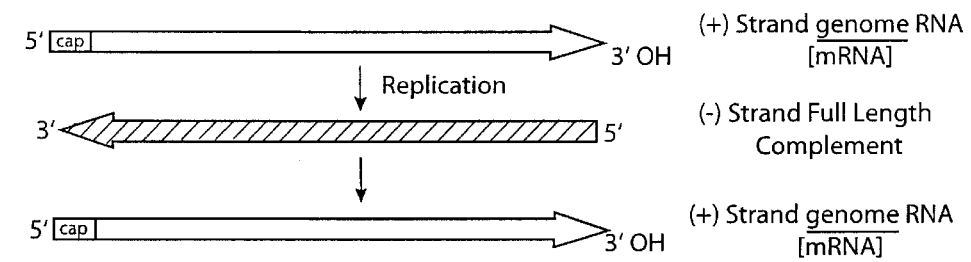
Figure 11D:
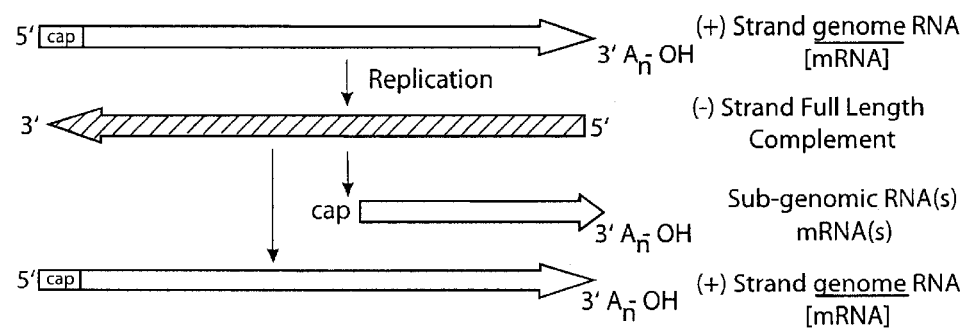

FIG. 9. Pol I-pol II system for the generation of human Parainfluenza virus III. The present invention may be used to produce parainfluenza III virus which comprises a negative strand, unimolecular RNA genome. Viral cDNA could be inserted into the pol I-pol II system either in a sense or an antisense orientation. In the figure the unidirectional system is presented. A pol I promoter directs synthesis of cRNA and a pol II promoter directs synthesis of mRNA. In this embodiment, a pol II promoter produces a polycistronic mRNA from which the first first open reading frame is efficiently translated into Nucleocapsid (NP) protein. This protein is required for replication. Plasmids encoding the L and P-protein, which are also essential for replication and transcription (but are not efficiently translated from the polycistronic mRNA), are prepared and are co-transfected on separate expression plasmids. Compared to the reverse genetics system developed by Durbin, A. P. et al., Virology 1997, 235 (2): 323–332, the pol I-pol II system has several advantages. By the expression of NP from the same cDNA, this minimum plasmid system requires the construction and transfection of only three instead of four plasmids to generate human Parainfluenzavirus III entirely from cloned cDNA. Unlike the reverse genetics systems based on the in vivo transcription from the T7-promoter, the pol I-pol II system is entirely driven by eucaryotic DNA dependent RNA polymerases found in each cell. Moreover, the infection of vaccinia virus which drives the expression of the T7 RNA polymerase requires the use of cells which are permissive for vaccinia virus (HeLa cells or derivatives such as Hep-2 cells) but not optimal for growth of human parainfluenza virus, thus limiting the utility of this approach for the generation of infectious virus. The severe cytopathic effects of vaccinia virus and the safety precautions required for use of infectious agents are undesireable features of this system. Use of the pol I-pol II system eliminates the requirement for a virus infection and allows the use of LLC-MK2 cells for transfection and growth of human Parainfluenza virus III, thus providing a technology for generating attenuated viruses in a simpler and safer way.

FIG. 10. Plasmid-based system for the generation of Rotavirus from cloned cDNA. This system can be used for generation of viruses with segmented, double stranded RNA genomes (e.g., Rotavirus). It can be applied, for example, to viruses which are members of the family Reoviridae (10, 11, 12 dsRNA segments) or Birnaviridae (2 dsRNA segments). To date, for viruses of the family Reoviridae, no reverse genetics systems are available. This figure illustrates how rotaviruses, which have 11 dsRNA segments, may be generated using the present invention, but similar systems can be employed for members of the genera Orbivirus (10 dsRNA segments) or Orthoreoviruses (12 dsRNA segments).

The following discussion illustrates the generation of the rotavirus A/SA11 entirely from cloned cDNA. All 11 segments of the simian rotavirus double stranded RNA genome have been determined. The dsRNAs in the genome are from 3302 bp to 663 bp long, and the size of the complete genome is 18,550 bp. The genome segments are numbered 1–11 in order of increasing mobility by PAGE (poly acrylamid gel electrophoresis) analysis. The segments are completely base-paired and the plus-sense strand contains a 5'-terminal cap structure (m7GpppGmGPy) but does not have a polyadenylation signal near its 3'-end. All genomic segments share short conserved 5' and 3' termini with a 10 nucleotide consensus at the 5'-end and an 8 nucleotide consensus at the 3'-end. Immediately internal to these terminal regions, in each gene, there is a second region of conservation of at least 30–40 nucleotides which are segment-specific. The 5'-non translated regions (NTRs) vary in length but are all less than 50 nucleotides and in all segments the NTRs are followed by at least one long open reading frame after the first AUG. Segments 9 and 11 encode two proteins. The 3'-NTRs vary in length ranging from 17 nts (segment 1) to 182 nts (segment 10).

Rotavirus cDNA is cloned into a dual promoter system, preferably a pol I-pol II system. After transfection of the resultant plasmids into a suitable host cell, viral RNAs and proteins are produced which results in formation of infectious rotavirus. Preferably, a unidirectional transcription system is used for producing rotavirus. Using this approach results in the intracellular synthesis of the 11 (+) RNA molecules of the rotaviral genome which have triphosphates at their 5' termini. Expression of virus-like mRNA results in expression of viral proteins. The viral protein VP3(cap), which has a guanylyltransferase and methyltransferase activity, catalyzes the addition of 5'-cap structures to all 11 rotaviral (+) RNA (Chen D., et al., Virology 1999, 265: 120–130). Indeed, it has been previously demonstrated that purified VP4(cap), a rotaviral VP3(cap) analogue of bluetogue virus (BTV), can add cap structures to a viruslike (+) RNA in vitro (Ramadevi N., et al. Proc Natl Acad Sci USA. 1998, 95 (23): 13537–42). It is anticipated that in vivo transcription of cDNA and VP3(cap) protein expression intracellularly, results in the generation of capped RNAs for all 11 rotaviral genomic segments. Those mRNAs are translated into viral proteins or are packaged into precore-RI. After the formation of VP6(T 13)-RI particles, the positive sense mRNA is used as template for the synthesis of (−)RNA. Ultimately, the addition of VP4 and VP7 during the morphogenesis results in infectious progeny virions.

Since the efficient initiation of replication and morphogenesis may be dependent on the optimal concentration of each of the viral proteins, it may be advantageous to generate separate plasmids for RNA synthesis and protein expression. However, because the level of protein expression can be optimized by varying the quantity of plasmids in the host cell or by use of different promoters for mRNA synthesis, use of two plasmids for one segment is not likely to be necessary for most of the genes. Since the (+) RNA is synthesized from a (−) RNA, the intracellular expression of (−) RNA and protein may result in the generation of replication competent units, which produce viral mRNA. Thus, the dual promoter system allows the establishment of a minimum plasmid system comprising a significantly lower number of plasmids than 22 which would be necessary if the RNA and protein expressing plasmids are on separate plasmids. Rotaviral generation may be performed in a similar manner to that used to produce influenza A virus.

FIGS. 11 A–D. Replication and mRNA synthesis of RNA virus genomes.

(A) mRNAs are synthesized by the viral polymerase proteins during infection of (−) strand viruses: One or two mRNAs for segmented RNA viruses or multiple mRNAs for viruses with unimolecular genomes. Antitermination mechanisms result in the synthesis of full length (+) strands, which can be copied into (−) genomic RNA.

(B) The segmented genomes of ambisense RNA viruses are copied to form one mRNA; a second RNA is synthesized from the complement.

(C) In cells infected with double-stranded RNA viruses, the mRNAs first synthesized can either be translated into protein or serve as templates for the synthesis of (−) strands, resulting in double-stranded genomic RNA.

(D) For (+) strand viruses, the genomic RNA is also an mRNA and is copied into (−) strand RNA, which can be copied into (+) genomic RNA. The mRNAs of some (+) RNA viruses do not contain a polyA tail. In some families one or more subgenomic RNAs are produced.

DETAILED DESCRIPTION

The life cycle of all RNA viruses includes RNA synthesis and assembly of virus particles after protein synthesis; these functions provide a conceptual framework for the reverse genetics systems of the present invention which may be used to produce RNA viruses from cloned cDNA. The present invention simplifies and improves currently available reverse genetics systems by establishing a dual promoter system for the production of negative strand segmented viruses (e.g., influenza A, influenza B, Bunyaviridae), non-segmented negative strand RNA viruses (e.g., Paramyxoviridae, Mononegavirales), double strand RNA viruses (e.g., Reoviridae, Birnaviridae) and positive strand RNA viruses (e.g., Flaviviridae, Picornaviridae, Coronaviridae, Togaviridae). Because the system of the present invention uses a single viral cDNA for both protein synthesis and genomic RNA synthesis, this systems reduces the number of plasmids required for virus production and allows the development of vaccines quickly and cheaply.

If a virus comprising a segmented RNA genome is to be produced using the present invention, a viral cDNA corresponding to each gene in the target genome is inserted into an expression plasmid of the invention. The invention comprises a bidirectional plasmid based expression system and a unidirectional plasmid based expression system wherein viral cDNA is inserted between an RNA polymerase I (pol I) promoter and terminator sequences (inner transcription unit). This entire pol I transcription unit is flanked by an RNA polymerase II (pol II) promoter and a polyadenylation site (outer transcription unit). In the unidirectional system, the pol I and pol II promoters are upstream of the cDNA and produce positive-sense uncapped cRNA (from the pol I promoter) and positive-sense capped mRNA (from the pol II promoter). The polI promoter, pol I terminator sequence, pol II promoter and polyadenylation signal in the unidirectional system may be referred to as comprising an "upstream-to-downstream orientation". In the bidirectional system, the pol I and pol II promoters are on opposite sides of the cDNA wherein an upstream pol II promoter produces positive-sense capped mRNA and a downstream pol I promoter produces negative-sense uncapped viral RNA (vRNA). These pol I-pol II systems start with the initiation of transcription of the two cellular RNA polymerase enzymes from their own promoters, presumably in different compartments of the nucleus. The pol I promoter and pol I terminator sequence in the bidirectional system may be referred to as comprising a "downstream-to-upstream orientation" whereas the pol II promoter and polyadenylation signal in the bidirectional system may be referred to as comprising an "upstream-to-downstream orientation".

If the target virus comprises a positive strand, segmented RNA genome, a pol I promoter is, preferably, located upstream of the cDNA in the inner transcription unit (unidirectional system). In this embodiment, positive strand RNA is generated for direct incorporation into new viruses. However, embodiments wherein target viruses comprise negative strand, segmented RNA genomes are produced using the unidirectional system are within the scope of the invention.

If the target virus comprises a negative strand, segmented RNA genome, the pol I promoter is, preferably, located downstream of the cDNA in the inner transcription unit (bidirectional system). In this embodiment, negative stranded RNA is generated for direct incorporation into new viruses. Embodiments wherein target viruses comprising positive stranded, segmented RNA genomes are produced with the bidirectional system are within the scope of the invention.

The present invention may also be used to produce viruses comprising infectious or uninfectious unsegmented RNA genomes (single stranded or double stranded). In general, simple introduction of infectious viral genomic RNA into a host cell is sufficient to cause initiation of the viral life cycle within the cell and the eventual production of complete viruses. For example, simple introduction of picornaviral genomic RNA into a host cell is sufficient to cause generation of complete picornaviruses. Initiation of the life cycle of a virus comprising uninfectious genomic RNA, typically, requires the additional introduction of other viral proteins which are usually carried within the viral particle along with the genome. For example, parainfluenza virus III carries an RNA dependent RNA polymerase whose presence is required within a newly infected host cell for initiation of viral genomic RNA replication and transcription of viral mRNAs; in the absence of the polymerase, parainfluenza III genomic RNA is not infectious. In embodiments of the present invention wherein viruses comprising infectious, unsegmented genomic RNAs are generated, simple introduction of a dual expression plasmid of the invention, carrying a nucleic acid including the viral genome, into a suitable host cell is sufficient to cause generation of complete viruses. In embodiments wherein viruses comprising uninfectious unsegmented genomic RNA are generated, additional expression plasmids may also have to be introduced into a host cell along with the dual expression plasmid carrying the viral genome. The additional plasmid should express the protein(s) required for initiation of the viral life cycle which are normally introduced into a host cell upon infection (e.g., RNA dependent RNA polymerases).

In embodiments wherein picornavirus, which comprising an infectious, unsegmented RNA genome, is produced, cDNA comprising the complete viral genome is inserted into a dual promoter expression plasmid of the invention. An upstream promoter in an outer transcription unit, preferably, a pol II promoter, directs production of a positive strand mRNA comprising the complete viral genome—a polyprotein is translated from the mRNA and individual proteins are cleaved and liberated from the polyprotein (e.g., by a protease within the polyprotein). Since the viral genome comprises positive strand RNA, a second upstream promoter in an inner transcription unit (unidirectional system), preferably pol I, directs production of a positive stranded copy of the genome. If the viral genome comprised negative strand RNA, a second downstream promoter, in an inner transcription unit (bidirectional system), preferably pol I, would direct production of a negative stranded copy of the genome. Embodiments wherein negative stranded, unsegmented RNA viruses are produced using the unidirectional system are within the scope of the invention. Similarly, embodiments wherein positive stranded, unsegmented RNA viruses are produced using the bidirectional system are within the scope of the invention.

Viruses comprising uninfectious, unsegmented RNA genomes wherein a polyprotein is not produced can also be generated with the present invention. For example, the present system may be used to produce rhabdoviridae viruses or paramyxoviridae viruses, preferably parainfluenza virus III, whose life cycle normally includes production of multiple monocistronic mRNAs from genomic, negative strand RNA by a virally derived RNA dependent RNA polymerase; individual proteins are expressed from the monocistronic mRNAs. In these embodiments, an outer transcription unit comprising a promoter, preferably a pol II promoter, directs production of a positive strand, polycistronic copy of the viral genome from which, generally, only the first gene (NP) is translated. Additionally, an inner transcription unit comprising a promoter, preferably a pol I promoter, directs expression of an RNA copy of the genome for incorporation into new viruses. Since the parainfluenza III viral genome comprises negative stranded RNA, the promoter of the inner transcription unit is preferably located downstream of the cDNA (bidirectional system). If the viral genome comprises positive strand RNA, the promoter of the inner transcription unit is preferably located upstream of the cDNA (unidirectional system). Embodiments wherein viruses comprising a positive stranded RNA genome are produced using the bidirectional system and embodiments wherein viruses comprising a negative stranded RNA genome are produced using the unidirectional system are within the scope of the invention. Additional viral proteins (other than the protein expressed from the polycistronic mRNA) are required for viral transcription and replication (L and P), and these proteins are provided individually on separate expression plasmids.

The invention may also include embodiments wherein viruses comprising double stranded, segmented RNA genomes are generated. In these embodiments, a plasmid comprising each gene in the target viral genome is inserted into a dual promoter expression plasmid of the invention. The plasmid may be either a unidirectional plasmid or a bidirectional plasmid. A promoter in an outer transcriptional unit, preferably a pol II promoter, directs expression of an mRNA transcript of each gene which is translated into the encoded protein. A promoter in an inner transcription unit, preferably a pol I promoter, directs transcription of either a positive strand (unidirectional system) or a negative strand (bidirectional system). Subsequently, the first strand which is produced may act as a template for production of the complementary strand by viral RNA polymerase. The resulting double stranded RNA product is incorporated into new viruses.

Recovery of the two influenza A viruses from a minimal plasmid-based system, A/WSN/33 (H1N1) and A/Teal/HK W312/97 (H6N1), established utility of this system. Recovery of a phenotypically indistinguishable A/PR/8/34 (H1N1) strain, which is the standard for production of inactivated influenza A vaccine, established the usefulness of this system for vaccine development. Seventy-two hours after the transfection of eight expression plasmids into co-cultured 293T and MDCK cells, the virus yield in the supernatant of the transfected cells was between $2\times10^5$ and $2\times10^7$ infectious viruses per ml. This eight-plasmid system was also used to generate single and quadruple reassortment viruses between A/Teal/HK/W312/97 (H6N1) and A/WSN/33 (H1N1), and to generate A/WSN/33 viruses from a tandem oriented system (which produces cRNA and mRNA).

Because the pol I-pol II system facilitates the design and recovery of both recombinant and reassortment influenza A viruses, it is also applicable to the recovery of other RNA viruses entirely from cloned cDNA. Although cDNA is preferred for use in the present invention, any other type of nucleic acid which encodes a viral gene which is to be expressed may be used if the essential elements of the invention are preserved. For example, PCR amplified products or restriction fragments comprising viral genes may be used. Furthermore, the genes expressed in the plasmid based system of the invention may be fused to or tagged with other genes such as purification/detection tags (e.g., glutathione-S transferase, polyhistidine, green fluorescent protein, myc tags and FLAG tags). The present invention also anticipates embodiments wherein partial gene sequences are used in plasmids of the present system.

The following table includes a non-limiting list of negative stranded RNA viruses which may be produced using the present invention:

| Order | Family | Subfamily | Genus | Type Species |
| --- | --- | --- | --- | --- |
| Mononegavirales | Bornaviridae | | Bornavirus | Borna disease virus |
| Mononegavirales | Filoviridae | | Ebola-like virus | Ebola virus |
| Mononegavirales | Filoviridae | | Marburg-like virus | Marburg virus |
| Mononegavirales | Paramyxoviridae | Paramyxovirinae | Respirovirus | Human parainfluenza virus 1 |
| Mononegavirales | Paramyxoviridae | Paramyxovirinae | Morbillivirus | Measles virus |
| Mononegavirales | Paramyxoviridae | Paramyxovirinae | Rubulavirus | Mumps virus |
| Mononegavirales | Paramyxoviridae | Pneumovirinae | Pneumovirus | Human Respiratory Syncitial Virus |
| Mononegavirales | Paramyxoviridae | Pneumovirinae | Metapneumovirus | Turkey Rhinotracheitis Virus |
| Mononegavirales | Rhabdoviridae | | Vesiculovirus | Vesicular Stomatitis Indiana Virus |
| Mononegavirales | Rhabdoviridae | | Lyssavirus | Rabies Virus |
| Mononegavirales | Rhabdoviridae | | Ephemerovirus | Bovine Ephemeral Fever Virus |
| Mononegavirales | Rhabdoviridae | | Novirhabdovirus | Infectious Hematopoietic Necrosis Virus |
| Mononegavirales | Rhabdoviridae | | Cytorhabdovirus | Lettuce Necrotic Yellows Virus |
| Mononegavirales | Rhabdoviridae | | Nucleorhabdovirus | Potato Yellow Dwarf Virus |
| Mononegavirales | Orthomyxoviridae | | Influenzavirus A | Influenza A Virus |
| Mononegavirales | Orthomyxoviridae | | Influenzavirus B | Influenza B Virus |
| Mononegavirales | Orthomyxoviridae | | Influenzavirus C | Influenza C Virus |
| Mononegavirales | Orthomyxoviridae | | Thogotovirus | Thogoto Virus |
| Mononegavirales | Bunyaviridae | | Bunyavirus | Bunyamwera Virus |
| Mononegavirales | Bunyaviridae | | Hantavirus | Hantaan Virus |
| Mononegavirales | Bunyaviridae | | Nairovirus | Nairobi Sheep Disease Virus |

-continued

| Order | Family | Subfamily | Genus | Type Species |
|---|---|---|---|---|
| Mononegavirales | Bunyaviridae | | Phlebovirus | Sandfly Fever Sicilian Virus |
| Mononegavirales | Bunyaviridae | | Tospovirus | Tomato Spotted Wilt Virus |
| Mononegavirales | Bunyaviridae | | Tenuivirus | Rice Stripe Virus |
| Mononegavirales | Bunyaviridae | | Ophiovirus | Citrus Psorosis Virus |
| Mononegavirales | Arenaviridae | | Arenavirus | Lymphocytic Chorio-meningitis Virus |
| Mononegavirales | Arenaviridae | | Deltavirus | Hepatitis Delta Virus |

The present invention is further based, in part, on development of a bidirectional transcription construct that contains viral cDNA encoding PB2, PB1, PA, HA, NP, NA, M or NS flanked by an RNA polymerase I (pol I) promoter for vRNA synthesis and an RNA polymerase II (pol II) promoter for viral mRNA synthesis. The utility of this approach is proved by the generation of virus after transfecting the pol I/pol II-promoter-PB1 construct together with vRNA- and protein-expression constructs for the remaining seven segments. Because this approach reduces the number of plasmids required for virus generation, it also reduces the work necessary for cloning, enhances the efficiency of virus generation and expands the use of the reverse genetics system to cell lines for which efficient cotransfection of 17 plasmids can not be achieved. Also included is a unidirectional transcriptional construct comprising pol I and pol II promoters placed upstream of a viral cDNA coding sequence. Both promoters are in a common upstream-to-downstream orientation in relation to the gene. Although the bidirectional system produces a higher influenza A viral titer, the unidirectional system is useful for other applications (e.g., production of other negative strand viral strains).

A promoter, terminator or polyadenylation signal is "upstream" of a gene if it is proximal to the start of the gene (e.g., the first codon) and distal to the end of the gene (e.g., the termination codon). A promoter, terminator or polyadenylation signal is "downstream" of a gene if it is proximal to the end of the gene and distal to the start of the gene. Promoters in the plasmids of the invention, which are functionally associated with a gene, are oriented so as to promote transcription of a sense or an antisense strand of the gene.

As used herein "expression plasmid" is a DNA vector comprising an "inner transcription unit" and an "outer transcription unit". As discussed above, expression plasmids may be used to generate any type of RNA virus, preferably positive or negative strand RNA viruses, segmented or unsegmented genome RNA viruses or double stranded RNA viruses. The outer transcription unit comprises a promoter, preferably a pol II promoter, which directs transcription, from a viral cDNA, of mRNA which is translatable. The outer transcription unit may comprise a T7 RNA polymerase promoter, a T3 RNA polymerase promoter, an SP6 RNA polymerase promoter or any promoter or combination of genetic elements capable of driving expression of a translatable RNA product. For example, the outer transcription unit may comprise a pol I or pol II promoter if the viral cDNA, which is to be expressed from the plasmid, is genetically engineered to include a polyadenylation signal at the 3' end of the transcribed RNA. This may be accomplished by inserting a string of A nucleotides at the 3' end of the cDNA coding sequence immediately before the stop codon. Furthermore, the viral cDNA can be genetically engineered to include an Internal Ribosomal Entry Site (IRES) at the 5' end of the cDNA to facilitate translational initiation from the transcribed RNA. An "inner transcription unit" in the expression plasmids of the invention is located within the outer transcription unit and comprises a promoter, preferably a pol I promoter, which can direct transcription of a viral cDNA which may be replicated by viral machinery and incorporated into new viruses. Preferably the promoter in the inner transcription unit transcribes RNA which does not comprise excess, non-virus extraneous, sequences at the 5' and 3' ends, preferably by precise fusion of viral cDNA with pol I promoter and terminator sequences. However, the invention includes embodiments wherein the inner transcription unit comprises a promoter which does direct production of RNA transcripts comprising 5' and 3' additional non-virus sequence (e.g., pol II promoters, pol III promoters, T7 RNA polymerase promoter, T3 RNA polymerase promoters or SP6 RNA polymerase promoters). In these embodiments, additional sequences may be included in the expression plasmid which ensure that RNA which is produced from the inner transcription unit do not include excess non-virus sequence. For example, the expression plasmid may be genetically engineered to include ribozymal sequences at the ends of transcripts produced from the inner transcription unit wherein the ribozymal portions of the transcribed RNA cleave the transcript in such a way that the sequences of the 5' and 3' termini of the RNAs are generated as found in the virus RNA. Furthermore, the expression plasmids may be genetically engineered to include terminator sequences which cause transcriptional termination at the end of the viral cDNA coding sequence thereby preventing incorporation of excess untranslatable sequences at the 3' end of the transcribed RNA. Preferably, an "expression plasmid" is a DNA vector employing the pol I-pol II system. Thus, such a plasmid comprises an RNA polymerase I (pol I) promoter and pol I terminator sequences, which are inserted between an RNA polymerase II (pol II) promoter and a polyadenylation signal. In the bidirectional system, an RNA polymerase I promoter controls expression of genomic negative sense uncapped RNA (termed herein "vRNA") of the cDNA which is inserted in an "antisense" orientation between the promoter and terminator. An RNA polymerase II promoter controls expression of messenger RNA; a viral gene cDNA segment inserted in a "sense" orientation between the pol II promoter and polyadenylation signal results in expression of positive-sense capped viral mRNA. In the unidirectional system, the viral cDNA is inserted downstream of the pol I and pol II promoters in a sense orientation. The pol II promoter drives the expression of positive-sense capped viral mRNA and the pol I promoter drives the expression of positive sense uncapped viral cRNA.

A plasmid may comprise "essentially all" of another base plasmid if all of the genes and functional non-coding regions of the base plasmid are present. For example, a plasmid constructed by mere removal of a portion of a polylinker and insertion of a foreign gene comprises essentially all of the base plasmid.

A "negative strand RNA virus" is a virus in which the viral genome comprises negative strand RNA. Negative strand RNA is complementary to mRNA and, generally, must be copied into the complementary positive strand mRNA for proteins to be translated. Typically, these viruses package an RNA dependent RNA polymerase for production of mRNA upon host cell infection. Negative strand RNA virus families include, but are not limited to, Orthomyxoviridae, Arenaviridae, and Bunyaviridae. Preferably, the viral genome is from a virus that is a member of the Orthomyxoviridae virus family, and optimally has a segmented genome. Members of the Orthomyxovirdae virus family include but are not limited to influenza A, influenza B, influenza C, Thogotovirus, Measles and Mumps viruses (Paramyxovirus) or Rhabies virus (Rhabdovirus).

A "positive strand RNA virus" is a virus comprising a positive strand RNA genome. Examples of positive stranded RNA viruses include Poliovirus (Picornavirus), Togaviruses and Flaviviruses. The genomic RNA of these viruses is the same sense as mRNA and may function as mRNA. These viruses may comprise a segmented or unsegmented genome.

A "double stranded RNA virus" comprises a double stranded RNA genome. Reoviruses are double stranded RNA viruses.

A viral genome may also be segmented or unsegmented unimolecular). A segmented genome comprises two or more nucleic acids each encoding one or more viral genes. Preferably, a segmented genome comprises a separate nucleic acid for each viral gene. Orthomyxoviruses (Influenza A, B or C virus), Bunyaviruses and Arenaviruses comprise segmented RNA genomes. A nonsegmented genome comprises a single nucleic acid comprising every viral gene. Mononegavirales viruses, Rhabdoviruses, Flaviviridae viruses, Picornaviridae viruses, Coronaviridea viruses, Togaviridae viruses and Paramyxoviruses comprise a nonsegmented RNA genome.

Double stranded RNA may be abbreviated as "dsRNA". Single stranded RNA may be abbreviated as "ssRNA." Single, negative strand RNA may be abbreviated as "−ssRNA". Single, positive strand RNA may be abbreviated as "+ssRNA."

A "viral gene segment" is, preferably, a cloned cDNA corresponding to a genomic RNA molecule from an RNA virus genome. This term may also include any gene or gene segment (e.g., a PCR product or restriction fragment) comprising a gene derived from an RNA virus.

A "minimum plasmid-based system" is a system in which there is an expression plasmid, as defined above, containing each autonomous viral genomic segment from an RNA virus. Thus, the total number of plasmids which contain viral genomic sequences will not exceed the total number of gene segments from the source RNA virus. The invention includes embodiments wherein other plasmids, which do not contain viral sequences, may optionally be cotransfected into the host cells. This provides significant advantages, by limiting the total number of plasmids required to establish the system in a host cell, eliminating the need for helper virus, eliminating the need for a selection process, and permitting efficient generation of reassortment viruses.

Certain viral genes in a minimum plasmid-based system of the invention can be from a viral strain well adapted to grow in cell culture, such as the PR/8/34 (H1N1) or WSN/33 (H1N1) strain, or from an attenuated strain, such as the A/Ann Arbor/6/60 (H2N2), or for influenza B/Ann Arbor/1/66. Preferably, an attenuated strain is also well adapted for growth in cell culture. In particular, for influenza A, preferred viral gene segments in the plasmid-based system encode viral polymerase complex proteins, M proteins, and/or NS proteins from a strain well adapted to grow in cell culture or from an attenuated strain, or both. These proteins are termed herein "viral internal proteins" or viral "non-glycoprotein".

The genome of influenza A virus typically encodes 10 different proteins: PB2, which is believed to be a transcriptase, PB1, which is believed to be a transcriptase, PA which is believed to be a transcriptase, HA which is believed to be hemeagglutinin, NP, which is believed to be an RNA binding nucleoprotein, NA which is believed to be neuramimidase, M1/M2 which are believed to be a matrix protein and an integral membrane protein, respectively, and NS1/NS2 which are believed to be nonstructural proteins which may affect RNA processing and transport. PB1, PB2, NP and PA are believed to be part of an influenza virus transcriptional polymerase complex.

The term "cell culture" as used herein preferably refers to a commercially acceptable method for propagating virus for vaccine production, e.g., embryonated hens' eggs, as well as to cell culture in vitro in a host cell (see Furminger, In: Nicholson, Webster and May (eds.), Textbook of Influenza, Chapter 24, pp. 324–332, particularly pp. 328–329).

Similarly, the plasmid-based system will incorporate gene segments for antigens required to produce a protective immunological response. A "protective immunological response" comprises a humoral (antibody) or cellular component, or both, effective to eliminate virions and infected cells in an immunized (vaccinated) subject. Thus, a protective immune response can prevent or resolve an RNA virus, e.g., influenza virus, infection. Preferably, the antigens are "surface antigens", i.e., expressed on the surface of the virion or the surface of infected cells. More preferably, the surface antigens are glycoproteins. For influenza, the primary glycoprotein antigens are hemagluttinin (HA or H) and neuramimidase (NA or N).

As used herein, the term "immunogenic" means that the polypeptide is capable of eliciting a humoral or cellular immune response, and preferably both. An immunogenic entity is also antigenic. An immunogenic composition is a composition that elicits a humoral or cellular immune response, or both, when administered to an animal. A molecule is "antigenic" when it is capable of specifically interacting with an antigen recognition molecule of the immune system, such as an immunoglobulin (antibody) or T cell antigen receptor. An antigenic polypeptide contains an epitope of at least about five, and preferably at least about 10, amino acids. An antigenic portion of a polypeptide, also called herein the epitope, can be that portion that is immunodominant for antibody or T cell receptor recognition, or it can be a portion used to generate an antibody to the molecule by conjugating the antigenic portion to a carrier polypeptide for immunization. A molecule that is antigenic need not be itself immunogenic, i.e., capable of eliciting an immune response without a carrier.

The term "pathogenic virus strain" is used herein to refer to any virus strain that is capable of causing disease; preferably, the virus is on the current World Health Organization (WHO), Centers for Disease Control and Prevention (CDC), or other public health authority list of likely circulating viruses. Such viruses may include members of the hepatitis virus family, reovirus family, orthomyxovirus family, the paramyxovirus family, the filoviridae family, the bornaviridae family, the bunyaviridae family, the arenaviridae family, coronaviridae family, poliovirus family or the rhabdovirus family. The invention advantageously provides for inserting the genes for the primary antigens from such strains into a plasmid-based system, in which the remaining viral genes have desired culture and/or attenuation characteristics, thus providing for production of quantities of virus of the appropriate antigenic background for vaccine production. For example, the genes of the paramyxovirus, human parainfluenza virus 3 (nucleocapsid gene, phosphoprotein gene, matrix gene, fusion gene, hemagglutinin-neuramimidase protein gene and large gene), may conveniently be placed in the plasmids of the invention for production of parainfluenza virus 3 virions.

Thus, a preferred "reassortment" virus of the invention is a virus in which gene segments encoding antigenic proteins from a pathogenic virus strain are combined with gene segments encoding viral polymerase complex or other similar genes (e.g., non-glycoprotein genes, including M genes and NS genes) from viruses adapted for growth in culture (or attenuated viruses). The reassortment virus thus carries the desired antigenic characteristics in a background that permits efficient production in a host cell, as described above. Such a reassortment virus is a desirable "virus seed" for production of virions to produce vaccine (see Furminger, supra).

The term "host cell" means any cell of any organism that is selected, modified, transformed, grown, or used or manipulated in any way, for the production of recombinant RNA virions, preferably negative strand segmented RNA virions, by the cell. Exemplary host cells include, but are not limited to, Madin-Darby Canine Kidney (MDCK) cells, VERO cells, CV1 cells, COS-1 and COS-7 cells, and BHK-1 cells, for example and not by way of limitation. In a specific embodiment, a transient co-culture is preferred for producing virions. Co-culturing permits efficient transfection of a receptive cell, such as a 293T cell, with subsequent infection of a permissive cell for viral growth, such as an MDCK cell.

The term "RNA virus virions" refers to the viral particles, which when first produced are fully infectious, from host cells transfected or co-transfected with a plasmid-based system of the invention. Such a system produces vRNA and viral proteins (from viral mRNA translation), resulting in assembly of infectious viral particles (virions).

As used herein, a "RNA virus-specific vaccine" is a composition that can elicit protective immunity to an RNA virus when administered to a subject. The term "vaccine" refers to a composition containing virus, inactivated virus, attenuated virus, split virus, or viral protein, i.e., a surface antigen, that can be used to elicit protective immunity in a recipient (see Furminger, supra). It should be noted that to be effective, a vaccine of the invention can elicit immunity in a portion of the population, as some individuals may fail to mount a robust or protective immune response, or, in some cases, any immune response. This inability may stem from the individual's genetic background or because of an immunodeficiency condition (either acquired or congenital) or immunosuppression (e.g., treatment with immunosuppressive drugs to prevent organ rejection or suppress an autoimmune condition). Efficacy can be established in animal models.

A "protective dose" of a vaccine is an amount, alone or in conjunction with an adjuvant, effective to elicit a protective immune response in a recipient subject. Protection can also depend on the route of administration, e.g., intramuscular (preferred for an inactivated vaccine) or intranasal (preferred for an attenuated vaccine).

The term "subject" as used herein refers to an animal that supports an RNA virus infection, including, but not limited to, water fowl, chickens, pigs, and humans. In particular, the term refers to a human.

An "adjuvant" is a molecule or composition that potentiates the immune response to an immunogen. An adjuvant is "acceptable for use in a human" when it is pharmaceutically acceptable, as defined below. Examples of adjuvants are provided below.

As used herein, the term "isolated" means that the referenced material is removed from its native environment, e.g., a cell. Thus, an isolated biological material can be free of some or all cellular components, i.e., components of the cells in which the native material occurs naturally (e.g., cytoplasmic or membrane component). A material shall be deemed isolated if it is present in a cell extract or supernatant. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified virion is preferably substantially free of host cell or culture components, including tissue culture or egg proteins, non-specific pathogens, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. Viral particles can be purified by ultrafiltration or ultracentrifugation, preferably continuous centrifugation (see Furminger, supra). Other purification methods are possible and contemplated herein. A purified material may contain less than about 50%, preferably less than about 75%, and most preferably less than about 90%, of the cellular components, media, proteins, or other nondesirable components or impurities (as context requires), with which it was originally associated. The term "substantially pure" indicates the highest degree of purity which can be achieved using conventional purification techniques known in the art.

In a specific embodiment, the term "about" or "approximately" means within 20%, preferably within 10%, and more preferably within 5% of a given value or range. Alternatively, logarithmic terms used in biology, the term "about" can mean within an order of magnitude of a given value, and preferably within one-half an order of magnitude of the value.

Genetic Engineering of Plasmid-Based Systems

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

These routine techniques apply to the preparation of pol I-pol II plasmid systems, isolation of viral gene segment cDNA clones, insertion of such DNAs into plasmids, and transfection of cells with a plasmid or plasmid-based system of the invention. In particularly, routine techniques of site-directed mutagenesis or gene modification permit modification of the RNA viral, preferably, negative strand segmented RNA viral genes to develop attenuated virus, as set forth below; or viral proteins that incorporate novel epitopes, e.g., in the neuramimidase stalk; or to create defective viruses.

"Amplification" of DNA as used herein denotes the use of polymerase chain reaction (PCR) to increase the amount of a particular DNA sequence within a mixture of DNA sequences. For a description of PCR see Saiki et al., Science 1988, 239: 487.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. A "recombinant DNA molecule" is a DNA molecule that has undergone a molecular biological manipulation.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins.

The polynucleotides herein may be flanked by heterologous sequences, including promoters, internal ribosome entry sites (IRES; Ghattas, et al., Mol. Cell. Biol. 11: 5848–5859, 1991) and other ribosome binding site sequences, enhancers, response elements, suppressors, signal sequences, polyadenylation sequences, introns, 5'- and 3'-noncoding regions, and the like. The nucleic acids may also be modified by many means known in the art. Non-limiting examples of such modifications include methylation, "caps" such as 5'-7-methyl-G(5')ppp(5')N caps, substitution of one or more of the naturally occurring nucleotides with an analog, and internucleotide modifications. Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "coding sequence" or a sequence "encoding" an expression product, such as a polypeptide, is a nucleotide sequence that, when expressed, results in the production of that polypeptide, i.e., the nucleotide sequence encodes an amino acid sequence for that polypeptide. A coding sequence for a protein may include a start codon (usually ATG) and a stop codon.

The term "gene", also called a "structural gene" means a DNA sequence that codes for or corresponds to a particular sequence of amino acids which comprise all or part of one or more polypeptides, and may or may not include regulatory DNA sequences, such as promoter sequences, which determine for example the conditions under which the gene is expressed.

In addition, the present invention permits use of various mutants, sequence conservative variants, and functionally conservative variants of RNA virus gene segments, preferably negative strand RNA virus gene segments, provided that all such variants retain the required immunoprotective effect. Indeed, the invention advantageously permits mutagenesis to develop attenuated viral strains in a systematic fashion.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein) expressed by a modified gene or DNA sequence. The term "variant" may also be used to indicate a modified or altered gene, DNA sequence, enzyme, cell, etc., i.e., any kind of mutant. Mutations can be introduced by random mutagenesis techniques, or by site-directed mutagenesis, including PCR-based sequence modification. As noted above, and discussed in detail below, mutagenesis of one or more individual gene segments of an RNA virus (e.g., a negative strand segmented RNA virus) permits development of attenuated viruses, as well as elucidation of the attenuation mechanism. Moreover, the plasmid-based system of the invention overcomes the drawbacks of prior efforts to develop attenuated viruses by mutagenesis, such as the restrictions of an efficient selection system (see Bilsel and Kawaoka, In: Nicholson, Webster and May (eds.), *Textbook of Influenza*, Chapter 32, pp. 422–434, especially pp. 423–425).

"Sequence-conservative variants" of a polynucleotide sequence are those in which a change of one or more nucleotides in a given codon position results in no alteration in the amino acid encoded at that position. Allelic variants can be sequence-conservative variants.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Some allelic variations result in functional-conservative variants, such that an amino acid substitution does not dramatically affect protein function. Similarly, homologous proteins can be function-conservative variants. Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms where the parameters are selected to give the largest match between the sequences tested, over the entire length of the reference sequence, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck, et al., Cell 50: 667, 1987). Such proteins (and their encoding genes) have sequence homology, as reflected by their sequence similarity, whether in terms of percent similarity or the presence of specific residues or motifs.

Accordingly, the term "sequence similarity" in all its grammatical forms refers to the degree of identity or correspondence between nucleic acid or amino acid sequences of proteins that may or may not share a common evolutionary origin (see Reeck, et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when a sufficient number of the nucleotides match over the defined length of the DNA sequences to differentiate the sequences from other sequences, as determined by sequence comparison algorithms, such as BLAST, FASTA, DNA Strider, and others where parameters are selected to give the largest match between the sequences tested, over the entire length of the reference sequence. Sequences that are substantially homologous can be identified by comparing the sequences using standard software available in sequence data banks, or in a Southern hybridization experiment under, for example, stringent conditions as defined for that particular system. Such stringent conditions are known to those skilled in the art and can be found in Current Protocols in Molecular Biology, John Wiley & Sons, N.Y. (1989), 6.3.1–6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., preferably at 55° C., and more preferably at 60° C. or 65° C.

Similarly, in a particular embodiment, two amino acid sequences are "substantially homologous" or "substantially similar" when enough of the amino acids are identical or similar (functionally identical) over a defined length to differentiate the sequences from other sequences. Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.). The following references regarding the BLAST algorithm are herein incorporated by reference: BLAST ALGORITHMS: Altschul, S. F., Gish, W., Miller, W., Myers, E. W. & Lipman, D. J., J. Mol. Biol. 215: 403–410, 1990; Gish, W. & States, D. J., Nature Genet. 3: 266–272, 1993; Madden, T. L., Tatusov, R. L. & Zhang, J., Meth. Enzymol. 266: 131–141, 1996; Altschul, S. F., Madden, T. L., Schäffer, A. A., Zhang, J., Zhang, Z., Miller, W. & Lipman, D. J., Nucleic Acids Res. 25: 3389–3402, 1997; Zhang, J. & Madden, T. L., Genome Res. 7: 649–656, 1997; Wootton, J. C. & Federhen, S., Comput. Chem. 17: 149–163, 1993; Hancock, J. M. & Armstrong, J. S., Comput. Appl. Biosci. 10: 67–70, 1994; ALIGNMENT SCORING SYSTEMS: Dayhoff, M. O., Schwartz, R. M. & Orcutt, B. C. (1978) "A model of evolutionary change in proteins." In "Atlas of Protein Sequence and Structure", vol. 5, suppl. 3. M. O. Dayhoff (ed.), pp. 345–352, Natl Biomed. Res. Found., Washington, D.C.; Schwartz, R. M. & Dayhoff, M. O. (1978) "Matrices for detecting distant relationships." In "Atlas of Protein Sequence and Structure", vol. 5, suppl. 3. M. O. Dayhoff (ed.), pp. 353–358, Natl. Biomed. Res. Found., Washington, D.C.; Altschul, S. F., J. Mol. Biol. 219: 555–565, 1991; States, D. J., Gish, W., Altschul, S. F., Methods 3: 66–70, 1991; Henikoff, S. & Henikoff, J. G., Proc. Natl. Acad. Sci. USA 89: 10915–10919, 1992; Altschul, S. F., J. Mol. Evol. 36: 290–300, 1993; ALIGNMENT STATISTICS: Karlin, S. & Altschul, S. F., Proc. Natl. Acad. Sci. USA 87: 2264–2268, 1990; Karlin, S. & Altschul, S. F., Proc. Natl. Acad. Sci. USA 90: 5873–5877, 1993; Dembo, A., Karlin, S. & Zeitouni, O., Ann. Prob. 22: 2022–2039, 1994 and Altschul, S. F. (1997) "Evaluating the statistical significance of multiple distinct local alignments." In "Theoretical and Computational Methods in Genome Research." (S. Suhai, ed.), pp. 1–14, Plenum, N.Y.

A "promoter sequence" is a DNA regulatory region capable of binding RNA polymerase in a cell and initiating transcription of a sequence. For purposes of defining the present invention, a promoter sequence which is located upstream of a cDNA is bounded at its 3' terminus by a transcription initiation site and extends upstream (5' direction) to include the minimum number of bases or elements necessary to initiate transcription at levels detectable above background. A promoter sequence which is located downstream of a cDNA (to express a (−)RNA) is bounded at its 5' terminus by a transcription initiation site and extends downstream (3' direction) to include the minimum number of bases or elements necessary to initiate transcription at levels detectable above background. The bidirectional system of the invention includes both upstream and downstream promoters; the unidirectional system includes only upstream promoters. Within the promoter sequence will be found a transcription initiation site (conveniently defined for example, by mapping with nuclease S1), as well as protein binding domains (consensus sequences) responsible for the binding of RNA polymerase.

Any known promoter may be used in the present invention as long as the essential elements of the invention are preserved. For example, pol II promoters that may be used to control gene expression include, but are not limited to, cytomegalovirus (CMV) promoter (U.S. Pat. Nos. 5,385,839 and 5,168,062), the SV40 early promoter region (Benoist and Chambon, Nature 290: 304–310, 1981), the promoter contained in the 3' long terminal repeat of Rous sarcoma virus (Yamamoto, et al., Cell 22: 787–797, 1980), the herpes thymidine kinase promoter (Wagner, et al., Proc. Natl. Acad. Sci. U.S.A. 78: 1441–1445, 1981), the regulatory sequences of the metallothionein gene (Brinster, et al., Nature 296: 39–42, 1982); T7 RNA polymerase promoters; T3 RNA polymerase promoters; SP6 RNA polymerase promoters and other promoters effective in the host cell of interest. Pol I promoters for expression of uncapped RNA are ubiquitous in all eukaryotes and include human RNA polymerase I (see *Molecular Cell Biology*, Darnell et al. eds 1986, pp. 311, 365–6). RNA polymerase III promoters may also be used in the present invention.

A coding sequence is "under the control of", "functionally associated with" or "operatively associated with" transcriptional and translational control sequences (e.g., a pol I or pol II promoter) in a cell when RNA polymerase transcribes the coding sequence into RNA, e.g., mRNA or vRNA.

The terms "express" and "expression" mean allowing or causing the information in a gene or DNA sequence to become manifest, for example producing an RNA (including cRNA, vRNA and virus mRNA) or protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell.

The term "transfection" means the introduction of a foreign nucleic acid into a cell so that the host cell will express the introduced gene or sequence to produce a desired polypeptide, coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Plasmids are preferred vectors of the invention.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes.

The term "expression system" means a host cell and compatible vector under suitable conditions, e.g. for the expression of a protein coded for by foreign DNA carried by the vector and introduced to the host cell.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, a gene encoding a polypeptide comprising a sequence from a library of sequences is heterologous to the vector DNA in which it is inserted for cloning or expression, and it is heterologous to a host cell containing such a vector, in which it is expressed.

As noted above, the invention permits generation of reassortment viruses using heterologous viral genes. In addition to incorporating genes for viral antigens in a genetic background of a virus strain adapted to grow well in culture, the invention permits creating cross-species reassortments, e.g., an influenza B antigen in an influenza A background.

Vaccines

As noted above, the present invention provides an efficient and economic strategy for production of vaccines for treating or preventing RNA viral infections, preferably, negative strand RNA virus infections. The minimal plasmid-based system of the invention eliminates the need for selection, and provides close control of reassortment viruses. For the production of an inactivated influenza vaccine six plasmids containing the non glycoprotein segments (e.g., PB1, PB2, PA, NP, M and NS) from a high yield strain (e.g., PR/8/34 (H1N1)) can be co-transfected with two expression plasmids containing the HA and NA cDNA of the recommended vaccine subtype. Since no helper virus is required, the generated virus is an influenza virus with the desired gene constellation. An analogous approach may be used to produce any variety of inactivated, reassortnent RNA virus for use in a vaccine. Expression plasmids comprising viral gene segments for a target virus (e.g, nonglycoprotein segments) may be cotransfected with other expression plasmids encoding proteins corresponding to a given infectious viral subtype (e.g, a viral subtype which is currently circulating in the population). Virus produced in accordance with the invention can be used in traditional or new approaches to vaccination (see Bilsel and Kawaoka, In: Nicholson, Webster and May (eds.), *Textbook of Influenza*, Chapter 32, pp. 422–434), particularly in the development of live, attenuated vaccines (discussed in greater detail infra). In particular, the present invention overcomes defects of current technology, with respect to development reassortment viruses with limited host range or unpredictable attenuation (id.).

Much efforts has gone into the development of influenza vaccines (see Wood and Williams, In: Nicholson, Webstern and May (eds.), *Textbook of Influenza*, Chapter 23, pp. 317–323). While much of this section relates to influenza vaccines, the scope of the present invention extends to all RNA virus vaccines, preferably, negative strand segmented RNA virus vaccines and particularly to Orthomyxoviridae vaccines.

Three types of inactivated influenza vaccines are currently available: whole virus, split-product, and surface antigen vaccines (see Wood, In: Nicholson, Webster and May (eds.), *Textbook of Influenza*, Chapter 25, pp. 333–345). Because the present invention permits the rapid development of a desired reassortment virus with acceptable growth characteristics in culture, it advantageously positions a vaccine manufacturer to generate a sufficient quantity of vaccine to meet public health needs and ensure standardization, which is an important requirement currently mitigated by the need to produce clinical quantities of vaccine, usually an 8 to 9 month period (Wood, supra, p. 333).

Vaccine safety is also a concern (see Wiselka, In: Nicholson, Webster and May (eds.), *Textbook of Influenza*, Chapter 26, pp. 346–357). Because the vaccines of the invention permit production in defined cell culture systems, they avoid non-specific pathogens, bacteria, and allergenic proteins that may be present in commercial vaccines prepared in embryonated eggs.

Adjuvants have been used with vaccines (e.g., influenza vaccines) (Wood and Williams, supra). The term "adjuvant" refers to a compound or mixture that enhances the immune response to an antigen. An adjuvant can serve as a tissue depot that slowly releases the antigen and also as a lymphoid system activator that non-specifically enhances the immune response (Hood, et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, and potentially useful human adjuvants such as BCG (bacille Calmette-Guerin) and *Corynebacterium parvum*. An example of a preferred synthetic adjuvant is QS-21. Alternatively, or in addition, immunostimulatory proteins, as described below, can be provided as an adjuvant or to increase the immune response to a vaccine. Preferably, the adjuvant is pharmaceutically acceptable.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Sterile water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Vaccination effectiveness may be enhanced by co-administration of an immunostimulatory molecule (Salgaller and Lodge, J. Surg. Oncol. 1998, 68: 122), such as an immunostimulatory, immunopotentiating, or pro-inflammatory cytokine, lymphokine, or chemokine with the vaccine, particularly with a vector vaccine. For example, cytokines or cytokine genes such as interleukin IL-1, IL-2, IL-3, IL-4, IL-12, IL-13, granulocyte-macrophage (GM)-colony stimulating factor (CSF) and other colony stimulating factors, macrophage inflammatory factor, Flt3 ligand (Lyman, Curr. Opin. Hematol., 5: 192, 1998), as well as some key costimulatory molecules or their genes (e.g., B7.1, B7.2) can be used. These immunostimulatory molecules can be delivered systemically or locally as proteins or by expression of a vector that codes for expression of the molecule.

Dendritic Cell Targeting. Vaccination may be accomplished through the targeting of dendritic cells (Steinman, J. Lab. Clin. Med., 128: 531, 1996; Steinman, Exp. Hematol., 24: 859, 1996; Taite et al., Leukemia, 13: 653, 1999; Avigan, Blood Rev., 13: 51, 1999; DiNicola et al., Cytokines Cell. Mol. Ther., 4: 265, 1998). Dendritic cells play a crucial role in the activation of T-cell dependent immunity. Proliferating dendritic cells can be used to capture protein antigens in an immunogenic form in situ and then present these antigens in a form that can be recognized by and stimulates T cells (see, e.g., Steinman, Exper. Hematol. 24: 859–862, 1996; Inaba, et al., J. Exp. Med., 188: 2163–73, 1998 and U.S. Pat. No. 5,851,756). For ex vivo stimulation, dendritic cells are plated in culture dishes and exposed to (pulsed with) virions in a sufficient amount and for a sufficient period of time to allow the viral antigens to bind to the dendritic cells. The pulsed cells can then be transplanted back to the subject undergoing treatment, e.g., by intravenous injection. Preferably autologous dendritic cells, i.e., dendritic cells obtained from the subject undergoing treatment, are used, although it may be possible to use MHC-Class II-matched dendritic cells, which may be obtained from a type-matched donor or by genetic engineering of dendritic cells to express the desired MHC molecules (and preferably suppress expression of undesirable MHC molecules.)

Preferably, the dendritic cells are specifically targeted in vivo for uptake of virus or viral subunits. Various strategies are available for targeting dendritic cells in vivo by taking advantage of receptors that mediate antigen presentation, such as DEC-205 (Swiggard et al., Cell. Immunol., 165: 302–11, 1995; Steinman, Exp. Hematol., 24: 859, 1996) and Fc receptors.

Inactivated Vaccines

Inactivated virus vaccines are well established for vaccinating against RNA virual infection (e.g., influenza) (see Nichol, In: Nicholson, Webster and May (eds.), *Textbook of Influenza*, Chapter 27, pp. 358–372). To prepare inactivated virus, the transfected virus is grown either in cell culture or in embryonated eggs. Virus can be inactivated treatment with formaldehyde, beta-propiolactone, ether, ether with detergent (such as Tween-80), cetyl trimethyl ammonium bromide (CTAB) and Triton N101, sodium deoxycholate and tri(n-butyl) phosphate (Furminger, supra; Wood and Williams, supra). Inactivation can occur after or prior to clarification of allantoic fluid (from virus produced in eggs); the virions are isolated and purified by centrifugation (Furminger, supra, see p. 326). To assess the potency of the vaccine, the single radial immunodiffusion (SRD) test can be used (Schild et al., Bull. World Health Organ. 1975, 52: 43–50 and 223–31 Mostow et al., J. Clin. Microbiol. 1975, 2: 531). The dose needed for a satisfactory immune response has been standardized and is 15 μg HA/strain/dose. The inactivated vaccine can be administered intramuscularly by injection.

Live Attenuated Influenza Vaccines

Attenuated cold adapted live RNA viral vaccines (influenza vaccines) have been developed (see Keitel and Piedra, In: Nicholson, Webster and May (eds.), *Textbook of Influenza*, Chapter 28, pp. 373–390; Ghendon, In: Nicholson, Webster and May (eds.), *Textbook of Influenza*, Chapter 29, pp. 391–399). The ability to generate influenza virus entirely from eight plasmids allows adjustment of the attenuation of a vaccine strain and enables development of a vaccine strain optimally suited for any target population (see, Bilsel and Kawaoka, supra). Because the influenza strains A/Ann arbor/6/60 (H2N2), or for influenza B/Ann Arbor/1/66, are used for preparation of live attenuated vaccines currently, one would insert each of the six cDNAs of the internal genes (PB2, PB1, PA, NP, M, NS) of the influenza into a plasmid such as pHW2000. Two plasmids containing the glycoproteins HA and NA of a relevant influenza strain would be constructed and co-transfected with the six master plasmids encoding the non-glycosylated influenza proteins.

It is expected that the genetic modification of the coding or noncoding region of the internal genes improves the safety, infectivity, immunogenicity and protective efficacy of the vaccine, in addition to permitting development of attenuated virus.

The manipulation of the HA gene can also increase the safety of a vaccine strain. For example, removal of basic amino acids found in the connecting peptide of H5 or H7 glycoproteins of highly pathogenic avian influenza A viruses can increase the safety of the vaccine.

Mucosal Vaccination. Mucosal vaccine strategies are particularly effective for many pathogenic viruses, since infection often occurs via the mucosa. The mucosa harbors dendritic cells, which are important targets for EBNA-1 vaccines and immunotherapy. Thus, mucosal vaccination strategies for inactivated and attenuated virus vaccines are contemplated. While the mucosa can be targeted by local delivery of a vaccine, various strategies have been employed to deliver immunogenic proteins to the mucosa.

In a specific embodiment, the vaccine can be administered in an admixture with, or as a conjugate or chimeric fusion protein with, cholera toxin, such as cholera toxin B or a cholera toxin A/B chimera (Hajishengallis, J Immunol., 154: 4322–32, 1995; Jobling and Holmes, Infect Immun., 60: 4915–24, 1992). Mucosal vaccines based on use of the cholera toxin B subunit have been described (Lebens and Holmgren, Dev Biol Stand 82: 215–27, 1994). In another embodiment, an admixture with heat labile enterotoxin (LT) can be prepared for mucosal vaccination.

Other mucosal immunization strategies include encapsulating the virus in microcapsules (U.S. Pat. No. 5,075,109, No. 5,820,883, and No. 5,853,763) and using an immunopotentiating membranous carrier (WO 98/0558). Immunogenicity of orally administered immunogens can be enhanced by using red blood cells (rbc) or rbc ghosts (U.S. Pat. No. 5,643,577), or by using blue tongue antigen (U.S. Pat. No. 5,690,938).

EXAMPLES

The present invention will be better understood by reference to the following examples, which illustrate the invention without limiting it.

Example 1

"Ambisense" Approach for the Generation of Influenza A Virus: vRNA and mRNA Synthesis from One Template As a first step in reducing the number of plasmids, this Example reports the construction and transfection of plasmids containing both the pol I and pol II-promoter on the same plasmid and presents evidence that this system allows the expression of vRNA and protein from one template. This Example has been published (Hoffmann et al., Virology 2000, 267: 310).

Materials and Methods

Cloning of plasmids. All cloning and PCR reactions were performed according to standard protocols. Briefly, the expression plasmids for the polymerase complex genes of A/WSN/33 were derived from pcDNA3 (Invitrogen) containing the immediate early promoter of the human cytomegalovirus (CMV) and the poly A site of the gene encoding bovine growth hormone (BGH). The viral cDNAs were derived from the plasmids pWNP143, pWSNPA3, pWSNPB2–14, pGW-PB1 to yield the expression constructs pHW25-NP, pHW23-PA, pHW21-PB2, pHW22-PB1. pHW12 was generated by inserting human pol I promoter and terminator sequences between the pol II-promoter and the polyA-site. The plasmid pHW52 was derived from pHW12 by first inserting oligonucleotides containing the noncoding region of PB1 extended by HindIII and XhoI sites and then inserting the PB1-coding region from pHW22-PB1 into these sites. The plasmid pHW82-PB1 was derived from pHW52-PB 1 by deletion of the CMV-promoter sequences. The coding region for the enhanced green fluorescent protein (EGFP) in the reporter construct pHW72-EGFP was obtained after PCR-amplification using pEGFP-N1 (Clontech) as template and inserting the cDNA after SacII/XhoI digestion into the plasmid pHW72 containing the human pol I promoter and murine terminator and the noncoding region of the M-segment separated by SacII/XhoI sites. pHW127-M and pHW128-NS were constructed by RT-PCR amplification of viral RNA with the primers containing segment specific sequences and BsmBI sites for insertion into the BsmBI digested vector pHH21 (E. Hoffmann, Ph.D. Thesis 1997, Justus Liebig University, Giessen, Germany; Neumann et al., Proc. Natl. Acad. Sci. USA 1999, 96: 9345). The construction of the plasmids pPolI-WSN-PB1; pPolI-WSN-PB2, pPolI-WSN-PA, pPolI-WSN-NP, pPolI-WSN-HA, pPolI-WSN-NA, pEWSN-HA, and pCAGGS-WNA15 has been described elsewhere (Neumann et al., supra).

Cell culture and transfection. Madin-Darby canine kidney (MDCK) cells were maintained in modified Eagle Medium (MEM) containing 10% fetal bovine serum (FBS), 293T human embryonic kidney cells were cultured in Dulbecco's modified Eagle medium (DMEM) containing 10% FBS. TransIT LT-1 (Panvera, Madison, Wis.) was used according to the manufacturer's instructions to transfect 1×106 293T cells. Different amounts of plasmids (Table 1) were mixed with TransIT LT-1 (2 µl TransIT LT-1 per 1 µg of DNA), incubated at room temperature for 45 min and added to the cells. Six hours later, the DNA-transfection mixture was replaced by Opti-MEM (Gibco/BRL, Gaithersburg, Md.) containing 0.3% bovine serum albumin (BSA) and 0.01% FBS. Forty-eight hours after transfection, supernatants containing virus were titrated in MDCK cells.

RNA isolation and RT-PCR. Viral RNA was isolated from virus particles with the use of the RNeasy-Kit (Qiagen, Valencia, Calif.) according to the manufacturer's instructions. For characterization of recombinant influenza viruses the Access RT-PCR kit (Promega, Madison, Wis.) was used according to the protocol provided. The following primers were used in the RT-PCR experiments: Seq-PB 1#1: 5'-AGG ATG GGA TTC CTC AAG G-3' (SEQ ID NO:1); Seq-PB1#2: 5'-GCT ATG GTT TCC AGA GCC CG-3' (SEQ ID NO:2); Bm-PB1-1: 5'-TAT TCG TCT CAG GGA GCG AAA GCA GGC A-3' (SEQ ID NO:3); Bm-PB1-2341R: 5'-ATA TCG TCT CGT ATT AGT AGA AAC AAG GCA TTT-3' (SEQ ID NO:4). RT-PCR experiments were performed by using the PTC-200 DNA engine (MJ Research, Watertown, Mass.). The amplification program started with 1 cycle at 48° C. for 45 min (first-strand cDNA synthesis), and 1 cycle at 94° C. for 2 min (inactivation of the AMV reverse transcriptase and cDNA denaturation). These cycles were followed by 40 cycles at 94° C. for 20 sec, 52° C. for 30 sec, and 72° C. for 30 sec (PCR amplification); the program ended with one cycle at 72° C. for 5 min. The PCR products were analyzed by agarose gel electrophoresis and sequenced with the primer Seq-PB1#1 or Seq-PB1#2.

Flow cytometry. Forty-eight hours after transfection, 293T cells were washed with phosphate-buffered saline (PBS), pelleted, and resuspended in PBS plus 5% FBS. Flow cytometric analysis was performed by using a FACS Calibur flow cytometer (Becton Dickinson) and the data were analyzed by using the CellQuest software package. For EGFP expression analysis we used the emission wavelength of 530 nm (FL1) to achieve a high sensitivity for EGFP mediated fluorescence detection.

RESULTS AND DISCUSSION

Design and features of the cloning vector pHW12 containing two eukaryotic promoters. Influenza A viruses are segmented viruses that contain RNA molecules with negative sense polarity. During the replication cycle, recognition of the 5'- and 3'-structures of the eight vRNA segments by the ribonucleoprotein complex proteins (PB2, PB1, PA, NP) results in the replication and transcription of the influenza virus genes. The fact that the terminal sequence elements are highly conserved indicates that a transcribed artificial RNA should have sequences that are the same as those of the 5'- and 3'-ends (Luo et al., J. Virol. 1991, 65: 2861; Flick et al., RNA 1996, 2: 1046). The cloning vector pHW12 was constructed, allowing the insertion of sequences of interest between the pol I promoter and terminator by using the restriction endonuclease BsmBI. The pol I transcription unit is flanked by the pol II promoter from the cytomegalovirus (CMV) and by the polyadenylation signal of the gene encoding bovine growth hormone. The CMV-promoter, the poly A site, and the backbone of the plasmid are derived from the cloning vector pcDNA3.

PB1 Protein Expression in the Pol I/Pol II Bidirectional Transcription System. To test the pol I/pol II one plasmid transcription system, cDNA of the PB1 gene of A/WSN/33 virus was inserted into the cloning vector pHW12 to yield the plasmid pHW52-PB1. HindIII and XhoI restriction sites were inserted into the 5' and 3' noncoding regions of this gene. These genetic tags were included to ensure that the generated recombinant virus could be identified by RT-PCR. We expected that human cells transfected with this plasmid would yield two types of RNA: PB 1-vRNA synthesized by cellular pol I and an mRNA with a 5'-cap structure synthesized by the pol II. Translation of the mRNA should result in the synthesis of PB 1-protein.

To examine whether the PB 1-protein is produced from this construct, we tested replication and transcription of an artificial vRNA by constructing the expression plasmids pHW21-PB2, pHW23-PA, and pHW25-NP, which contain cDNAs encoding PB2, PA and NP proteins of A/WSN/33 under the control of the CMV-promoter. For the in vivo synthesis of an artificial vRNA, we constructed the reporter plasmid pHW72-EGFP, containing the EGFP cDNA flanked by the noncoding region of the M-segment and the human pol I-promoter and the murine terminator sequence. Five plasmids (2 µg pHW21-PB2, 2 µg pHW52-PB 1 (pol I/pol II promoter construct), 2 µg pHW23-PA, 2 µg pHW25-NP, and 1 µg pHW72-EGFP) were transfected into 293T cells. Twenty-four and 48 h after transfection, the cells were analysed by fluorescence microscopy. After 24 hours fluorescent cells were observed. This result shows that within 24 hours the polymerase proteins are synthesized in a concentration sufficient to allow recognition of the influenza virus specific ends of the EGFP-vRNA. These proteins synthesize mRNA which is translated into EGFP.

To evaluate the efficiency of this system, we performed flow cytometric analysis to count the number of fluorescent cells. Forty-eight hours after transfection of the five plasmids, 18.72% of the cell population showed fluorescence. Only a background level of fluorescent cells (0.06%) was observed when pHW52-PB1 plasmid was not added; this finding is consistent with those of earlier studies showing that all four RNP complex proteins are necessary for the amplification of the vRNA (Huang et al., J. Virol. 1990, 64: 5669). The results indicate that the PB1-cDNA transcription and the resulting concentration of PB 1 protein together with the other RNP complex proteins is sufficient to initiate a viral transcription/replication process.

Generation of recombinant influenza A virus. For the generation of infectious influenza A virus, it is necessary that the plasmid pHW52-PB1 provides not only PB1 mRNA and protein but also sufficient amounts of PB1-vRNA, which can be packaged into progeny virus. For the remaining seven vRNAs, we used plasmids that contain the cDNAs for the full-length RNAs of the A/WSN/33 virus, flanked by the human pol I promoter and the murine terminator. Transfection of these plasmids should result in the synthesis of all eight viral RNAs that are replicated and transcribed by the polymerase proteins forming new vRNPs. After synthesis of the structural proteins, the RNPs would be packaged into new virus particles.

We transfected 293T cells with different amounts of pHW52-PB1 plasmid (0, 2, 4 µg) together with the plasmids pPolI-WSN-PB2, pPolI-WSN-PA, pPolI-WSN-HA, pPolI-WSN-NP, pPolI-WSN-NA, pHW127-M, pHW128-NS (1 µg each). The protein expression plasmids pHW21-PB2 (1 µg), pHW23-PA (0.1 μg), pHW25-NP (1 μg), pEWSN-HA (1 μg), and pCAGGS-WNA15 (1 μg) were cotransfected. The expression plasmids for the hemagglutinin (HA) and the neuramimidase (NA) were included to increase the yield of transfectant virus.

Forty-eight hours after transfection, the supernatant of the primary transfected 293T cells was transferred to MDCK cells. In all transfection experiments in which pHW52—PB 1 plasmid was added, 24 hours after the passage we observed a virus-induced cytopathic effect. No cytopathic effect was visible if no PB 1 expressing plasmid was included in the transfection reaction. The virus titer was determined by titrating the supernatant of the transfected cells on MDCK cells; the supernatant was found to contain $2\times10^4$–$2\times10^5$ pfu/ml. This finding shows that after transfection of the PB1-pol I/pol II-promoter plasmid (together with the expression plasmids) PB1 vRNA and PB1 protein are synthesized in the human cell line 293T at a level sufficient for the generation of infectious influenza A viruses. In the cotransfection experiments with plasmids containing the PB1-cDNA separated on two plasmids (pHW82-PB1 and pHW22-PB1), a virus titer of $2\times10^4$ pfu/ml was found; the analogous experiment using the plasmids with wild-type PB1 sequences (pPol I-WSN-PB1 and pHW22-PB1) resulted in a virus titer of $3\times10^6$ pfu/ml.

Unlike the expression construct with a pol II-promoter used in a previous study (Neumann et al., Proc. Natl. Acad. Sci. USA 1999, 96: 9345), we used the plasmid pHW52-PB1 that contains sequences derived from the pol I-transcription unit that are inserted between the CMV-promoter and the polyadenylation site. The expression of the EGFP reporter gene demonstrates that the overall expression of PB1-protein in this system is sufficient for formation of EGFP-RNP complexes. Although the pol I-promoter/terminator region contains recognition sequences for pol I specific transcription and termination factors (Beckmann et al., Science 1995, 270: 1506; Bell et al., Science 1988, 241: 1192; Kuhn et al., EMBO J. 1994, 13: 416), these DNA binding proteins do not seem to inhibit pol II-mediated transcription. These findings are consistent with the finding that the pol I-specific DNA binding proteins are more abundant in the nucleolus, the compartment in which the cellular rDNA-transcription takes place (Evers et al., EMBO J. 1995, 14: 1248). These results indicate that after transfection of the pol I/pol II-promoter construct into the cell, some of the plasmids are delivered to the nucleolus, where the pol I-mediated transcription occurs and some are retained in the nucleus, where they are transcribed by RNA polymerase II.

Because the reporter construct pHW52-PB1 contained additional non-influenza virus sequences (restriction sites) in the noncoding region before the start codon and after the stop codon, we were interested whether these sequences were stably maintained in the viral PB1 RNA segment. Therefore, we isolated vRNA after the second passage of transfectant virus on MDCK cells and performed reverse transcription-PCR analysis. The amplification of vRNA with PB1-specific primers resulted in the generation of cDNA-fragments of the expected sizes. With the same viral RNA and primers, but without the addition of reverse transcriptase, no amplification product was obtained, showing that the cDNA originated from viral RNA and not from plasmid DNA carried over from the supernatant of transfected cells.

Sequencing of the PCR-products revealed that both restriction site sequences were present in the RNA molecule. The results show that the pol I/pol II transcription system allows recovery of infectious recombinant virus and that virus with foreign sequences in the noncoding region of the PB1 gene is viable. This modified PB1-segment is still replicated, transcribed, and packaged into virus particles. Previously, by using the RNP transfection system the non-coding region of influenza A virus segments were changed. By substituting the noncoding region of the NA gene with the corresponding sequence of the NS-segment of influenza B transfectant influenza viruses were obtained (Muster et al., Proc. Natl. Acad. Sci. USA 1991, 88: 5177; Bergmann and Muster, J. Gen. Virol. 1995, 76: 3211). This type of virus with a chimeric NA segment showed an attenuated phenotype in mice and protected mice inoculated with a non lethal dose against infection of the wild-type influenza virus infection. These results showed that the genetic alteration of the noncoding region of an RNA segment can change the biologic property of a transfectant virus. Here, we report for the first time that even non-influenza virus sequences can be inserted into the noncoding region of the PB1 segment.

With the pol I/pol II transcription system it is now possible to systematically modify these sequence elements in the noncoding region of the PB1 segment and to evaluate whether these genetic manipulations result in changes in the biologic properties of the recombinant viruses. Indeed, the lower yield of the viruses with the mutated PB1 segment compared to the wild-type virus indicates that the inserted sequences negatively influence the virus growth.

Although the plasmid-based system developed recently (Neumann et al., supra) is highly efficient in generating influenza virus, it involves cloning 14–17 plasmids. In this study we reduced the number of plasmids to 13 needed for the efficient recovery of influenza A/WSN/33 virus strain. The reduction in the number of plasmids achieved by this approach promises to increase the efficiency of transfection for cell lines other then 293T cells, thus allowing the delivery of genes to cell lines for which the efficient delivery of 14 plasmids is difficult to achieve. Fodor et al. (J. Virol. 1999, 73: 9679) were able to rescue influenza virus after transfecting 12 plasmids, but the virus yield in that study was only 1–2 infectious virus particles per $10^6$ transfected Vero cells.

Example 2

Construction of Recombinant Influenza A Viruses From a Minimal Plasmid-Based System This example describes use of the plasmid-based transfection system for the rescue of influenza A virus entirely from cloned cDNA. Unlike established plasmid-based systems, this system for the generation of influenza A virus employs the construction and transfection of only eight expression plasmids, each containing one copy of a different viral cDNA corresponding to a viral gene segment. This reverse-genetics system reduces the number of plasmids required for the recovery of influenza A viruses and allows the predictable and efficient generation of reassortment viruses.

Materials and Methods

Cloning of plasmids. The plasmid pHW2000 (FIG. 3A) was derived from pHW12 (Example 1). The pHW2000 cloning vector contains 225 bp of the human pol I promoter and 33 bp of the murine terminator sequence separated by two BsmBI sites. The pol I promoter and terminator elements are flanked by a truncated immediate-early promoter of the human cytomegalovirus (starting approximately 350 bp upstream of the transcription start site as found in pcDNA3, Invitrogen, Carlsband, Calif.) and by the polyadenylation signal of the gene encoding bovine growth hormone. The eight plasmids containing the cDNA of the virus A/WSN/33 (H1N1) (pHW181-PB2, pHW182-PB1, pHW183-PA, pHW184-HA, pHW185-NP, pHW186-NA, pHW187-M, and pHW188-NS) were constructed by inserting ApaI-SalI fragments (with viral cDNA and pol I promoter and terminator sequences) of the plasmids pPolI-WSN-PB2, pPolI-WSN-PB1, pPolI-WSN-PA, pPolI-WSN-NP, pPolI-WSN-HA, pPolI-WSN-NA (Neumann et al., Proc. Natl. Acad. Sci. USA 1999, 96: 9345), pHW127M, and pHW128-NS (Example 1) into the ApaI-SalI vector fragment of pHW2000. The eight plasmids containing the cDNA of A/Teal/HK/W312/97 (H6N 1) (pHW241-PB2, pHW242-PB1, pHW243-PA, pHW244-HA, pHW245-NP, pHW246-NA, pHW247-M, and pHW248-NS) were constructed by reverse-transcriptase polymerase chain reaction (RT-PCR) amplification of the viral RNA. The primers used in the PCR reaction contained segment-specific sequences at their 3' end and BsmBI or BsaI restriction site sequences at their 5' end. After digestion of the PCR products with BsmBI or BsaI, the fragments were cloned into the vector pHW2000 (FIG. 3A). The sequences of the primers used for amplification of the genome of A/teal/HK/W312/97 (H6N1) follow. The primers are shown from left to right corresponding to the 5' and 3' ends. The influenza A specific nucleotides are underlined.

experiments six well tissue culture plates were used. The day before transfection confluent 293T and MDCK cells in a 75 $cm^2$ flask were trypsinized and 10% of each cell line was mixed in 18 ml OptiMEM I; 3 ml of this cell suspension was seeded into one well of a six well plate. The cocultured MDCK and 293T cells (0.2–1×$10^6$ cells per well each) were used for the transfection experiments. TransIT LT-1 (Panvera, Madison, Wis.) was used according to the manufacturer's instructions to transfect the cells. Briefly, 2 μl of TransIT LT-1 per 1 μg of DNA was mixed, incubated at room temperature for 45 min, and added to the cells. Six hours later, the DNA-transfection mixture was replaced by Opti-MEM I. Thirty hours after transfection, 1 ml of Opti-MEM I containing TPCK-trypsin was added to the cells; this addition resulted in a final concentration of TPCK-trypsin of 0.5 μg/ml in the cell supernatant. The virus titer of the cell supernatant was determined by titration of the supernatant on MDCK cells.

RNA isolation and RT-PCR. Viral RNA was isolated from virus particles with the RNeasy-Kit (Qiagen, Valencia, Calif.), which was used according to the manufacturer's instructions. For characterization of recombinant influenza viruses, the Access RT-PCR kit (Promega, Madison, Wis.) was used according to the protocol provided. The following primers were used in the RT-PCR experiments: Bm-NS#1 (5'-TAT TCG TCT CAG GGA GCA AAA GCA GGG TG-3;

```
NS:
Bm-NS#1:       TATTCGTCTCAGGGAGCAAAAGCAGGGTG          (SEQ ID NO:5)
Bm-NS#2:       ATATCGTCTCGTATTAGTAGAAACAAGGGTGTTT     (SEQ ID NO:6)

M:
Bm-M#1:        TATTCGTCTCAGGGAGCAAAAGCAGGTAG          (SEQ ID NO:7)
Bm-M#2:        ATATCGTCTCGTATTAGTAGAAACAAGGTAGTTTTTT  (SEQ ID NO:8)

NA:
Bm-NA1-1:      TATTCGTCTCAGGGAGCAAAAGCAGGAGTTTAACATG  (SEQ ID NO:9)
Bm-NA-1413R:   ATATCGTCTCGTATTAGTAGAAACAAGGAGTTTTT    (SEQ ID NO:10)

HA:
Bm-H6-1:       TATTCGTCTCAGGGAGCAAAAGCAGGGGAAAATG     (SEQ ID NO:11)
Bm-NS#2:       ATATCGTCTCGTATTAGTAGAAACAAGGGTGTTT     (SEQ ID NO:6)
(note: HA and NS segment have the identical
sequence in this part of the noncoding region)
NP:
Ba-NP-1:       TATTGGTCTCAGGGAGCGAAAGCAGGGTA          (SEQ ID NO:12)
Ba-NP1565R:    ATATGGTCTCGTATTAGTAGAAACAAGGGTATT      (SEQ ID NO:13)

PA:
Bm-PA1-1:      TATTCGTCTCAGGGAGCGAAAGCAGGTACTGATCC    (SEQ ID NO:14)
Bm-PAI-2231R:  ATATCGTCTCGTATTAGTAGAAACAAGGTACTTTTT   (SEQ ID NO:15)

PB1:
Bm-PB1a-1:     TATTCGTCTCAGGGAGCGAAAGCAGGCAAACC       (SEQ ID NO:16)
Bm-PB1-2341R:  ATATCGTCTCGTATTAGTAGAAACAAGGCATTT      (SEQ ID NO:4)

PB2:
Ba-PB2-1:      TATTGGTCTCAGGGAGCGAAAGCAGGTCAATTATATTC (SEQ ID NO:17)
Ba-PB2-2341R:  ATATGGTCTCGTATTAGTAGAAACAAGGTCGTTTTT   (SEQ ID NO:18)
```

The RT-reaction was performed with the primer 5'-AGCAAAAGCAGG-3'(SEQ ID NO:19). To ensure that the viral cDNAs derived from RT-PCR amplification in the expression plasmids did not have unwanted mutations, the inserted cDNAs were sequenced.

Viruses and cell culture. Influenza viruses A/WSN/33 (H1N1) and A/Teal/HK/W312/97 (H6N 1) were propagated in 10-day-old eggs. Madin-Darby canine kidney (MDCK) cells were maintained in modified Eagle Medium (MEM) containing 10% FBS. 293T human embryonic kidney cells were cultured in Opti-MEM I (Life Technologies, Gaithersburg, Md.) containing 5% FBS. For the transfection SEQ ID NO:5) and Bm-NS#2 (5'-ATA TCG TCT CGT ATT AGT AGA AAC AAG GGT GTT TT-3; SEQ ID NO:6). RT-PCR experiments were performed by using the PTC-200 DNA engine (MJ Research, Watertown, Mass.). The amplification program started with 1 cycle at 48° C. for 45 min and 1 cycle at 94° C. for 2 min. These cycles were followed by 40 cycles at 94° C. for 20 sec, 52° C. for 30 sec, and 72° C. for 40 sec; the program ended with one cycle at 72° C. for 5 min. The PCR products were analyzed by agarose gel electrophoresis and sequenced with the primer Bm-NS#1. The Center for Biotechnology at St. Jude Children's Research Hospital determined the sequence of template DNA by using rhodamine or dRhodamine dye-terminator cycle sequencing ready reaction kits with AmpliTaq® DNA polymerase FS (Perkin-Elmer, Applied Biosystems, Inc. [PE/ABI], Foster City, Calif.) and synthetic oligonucleotides. Samples were subjected to electrophoresis, detection, and analysis on PE/ABI model 373, model 373 Stretch, or model 377 DNA sequencers.

RESULTS

Figure 2:
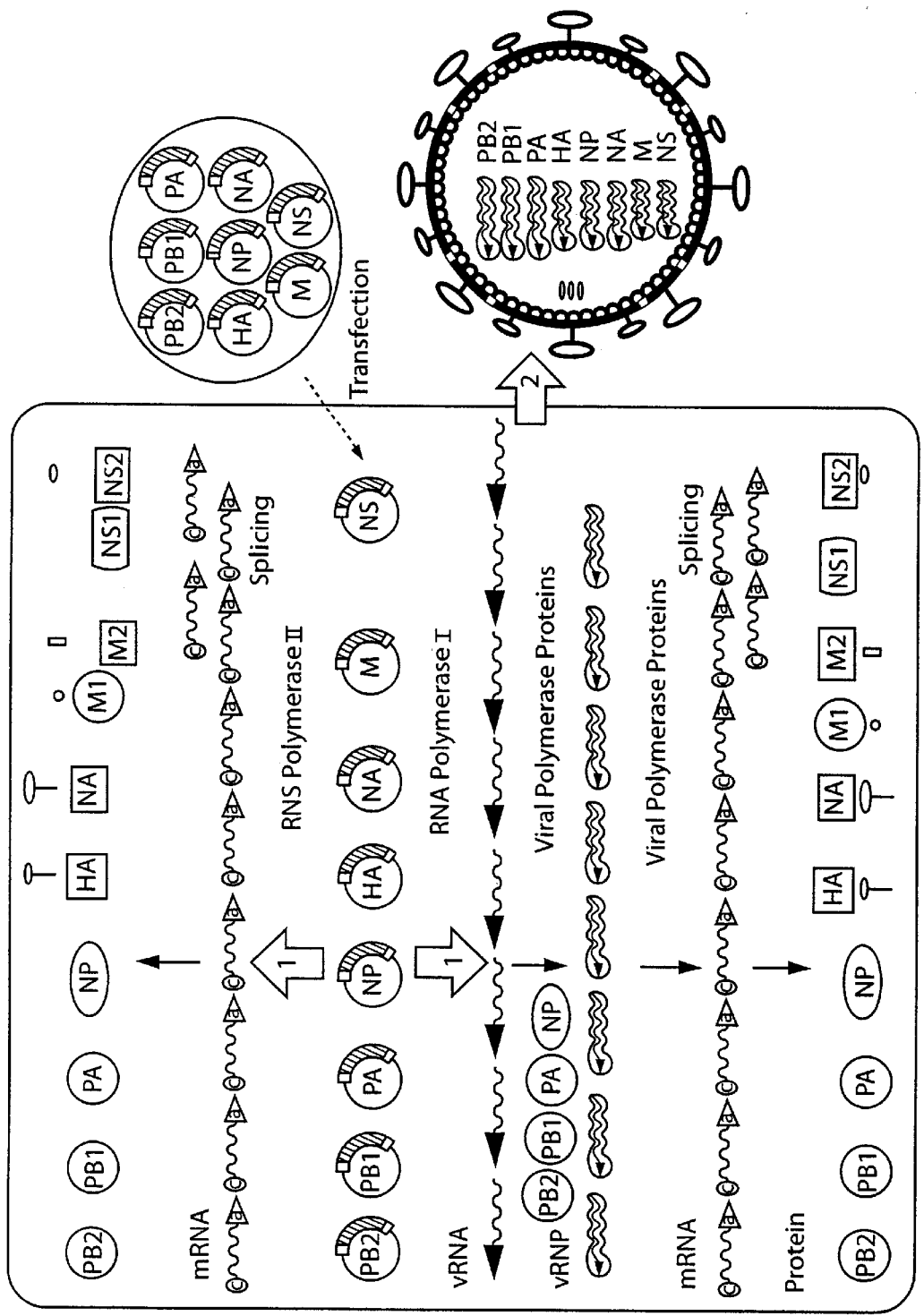
FIG. 2. The eight plasmid pol I-pol II system for the generation of influenza A virus. Eight expression plasmids containing the eight viral cDNAs inserted between the human pol I promoter and the pol II promoter (see FIG. 1) are transfected into eukaryotic cells. Because each plasmid contains two different promoters, both cellular pol I and pol II will transcribe the plasmid template, presumably in different nuclear compartments, which results in the synthesis of viral mRNAs and vRNAs. After synthesis of the viral polymerase complex proteins (PB1, PB2, PA, NP), the viral replication cycle is initiated. Ultimately, the assembly of all viral molecules directly (pol II transcription) or indirectly (pol I transcription and viral replication) derived from the cellular transcription and translation machinery results in the interaction of all synthesized molecules (vRNPs and the structural proteins HA, NA, M1, M2, NS2/NEP) to generate infectious influenza A virus.

Establishment of the pol I-pol II system for the generation of A/WSN/33 (H1N1). Because the genome of influenza A virus contains eight segments, it was reasoned that the insertion of all eight influenza A cDNAs between a pol I promoter and a pol II promoter should result in the transcription of the eight vRNAs, all viral in RNAs, and in the synthesis of all 10 viral proteins (FIG. 1). After assembly of all viral ribonucleoproteins with the structural proteins, infectious influenza A virus should then be formed (FIG. 2).

Figure 4A:
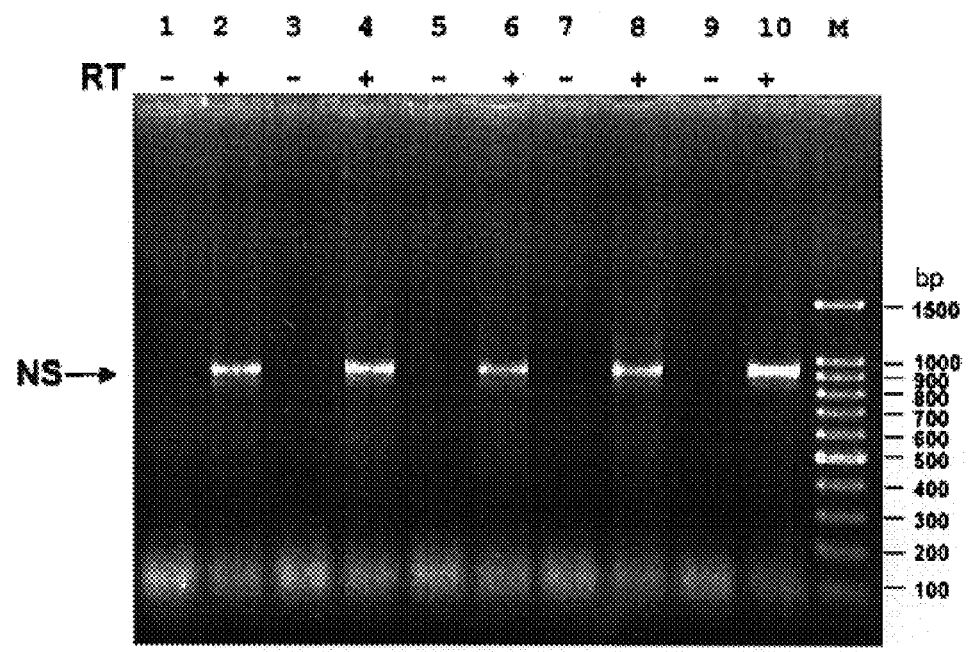
FIGS. 4A and 4B. Characterization of the recovered viruses by RT-PCR. A. RNA was extracted from virus particles after two passages of the supernatant of transfected cells (see Tables 1 and 2) on MDCK cells. RT-PCR was performed with primers specific for the NS gene segment and with vRNA extracted from virions. The NS primers used were not strain specific; thus, allowing the amplification of any influenza A NS segment. The reaction products were subjected to electrophoresis on a 2% agarose gel. To ensure that the amplified DNA fragments were derived from vRNA and not from plasmid DNA carried over from transfected cells, one reaction was performed without the addition of reverse transcriptase (RT) (−). Lanes 1 and 2, recombinant A/Teal/HK/W312,97 (Table 1); lanes 3 and 4, M-reassortment (Table 2); Lanes 5 and 6, NS-reassortment (Table 2); lanes 7 and 8, recombinant A/WSN/33 virus (Table 1); lanes 9 and 10, quadruple-reassortment (Table 2). B. NcoI digestion of the fragments shown in A. The identity of the NS fragments was also verified by sequence analysis of the amplified product (not shown).
Figure 4B:
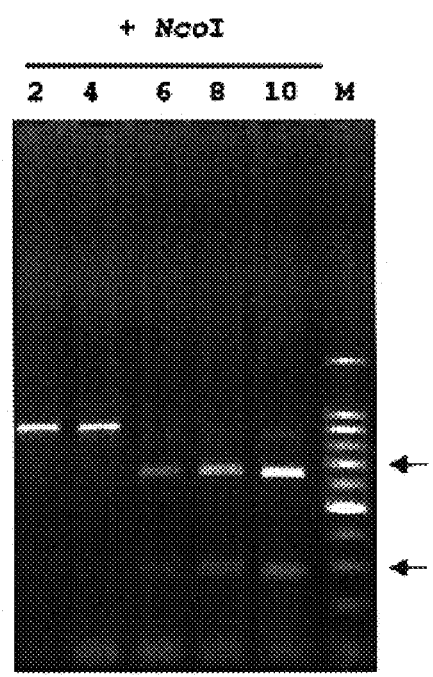

To test whether infectious influenza A virus could be rescued with this cDNA-bidirectional transcription system, the eight expression plasmids (pHW181-PB2, pHW182-PB1, pHW183-PA, pHW184-HA, pHW185-NP, pHW186-NA, pHW187-M, and pHW188-NS) were constructed containing the eight cDNAs of A/WSN/33 (H1N1). Eight plasmids (1 µg of each plasmid) (Table 1) were cotransfected into transiently cocultured 293T-MDCK cells. Both cell lines were cocultured in one cell-culture well the day before transfection to ensure conditions for high DNA transfection efficiency (293T cells) and for replication efficiency (MDCK cells) of influenza A viruses. After 48 and 72 hours, the MDCK cells showed a virus-induced cytopathic effect, but no cytopathic effect was observed after transfection of seven plasmids without the PB1-expression construct (Table 1). The virus titer of the supernatant was determined at different times posttransfection by titration in MDCK cells. Twenty-four hours posttransfection cell supernatant contained $1 \times 10^3$ viruses per ml; $2 \times 10^7$ infectious viruses were generated 72 hours posttransfection (Table 1) per ml. The recovered viruses were passaged two times on MDCK cells. To verify that the generated virus was the designed A/WSN-virus, the cDNA was produced for the NS gene by RT-PCR (FIG. 4A, lane 8). The generation of two fragments after digestion with the restriction endonuclease NcoI (FIG. 4B, lane 8) and sequence analysis of the amplified fragment confirmed that the recovered virus was indeed the designed A/WSN virus. These findings show that the pol I and pol II-driven synthesis of vRNA and mRNA from eight templates results in the generation of infectious influenza A virus.

TABLE 1

Plasmid sets used for the recovery of A/WSN/33 (H1N1) and A/Teal/HK/W312/97 (H6N1) Viruses

| Segment | A/WSN/33 (H1N1) | | A/Teal/HK/W312/97 (H6N1) | |
|---|---|---|---|---|
| 1 | pHW181-PB2 | pHW181-PB2 | pHW241-PB2 | pHW241-PB2 |
| 2 | — | pHW182-PB1 | — | pHW242-PB1 |
| 3 | pHW183-PA | pHW183-PA | pHW243-PA | pHW243-PA |
| 4 | pHW184-HA | pHW184-HA | pHW244-HA | pHW244-HA |
| 5 | pHW185-NP | pHW185-NP | pHW245-NP | pHW245-NP |
| 6 | pHW186-NA | pHW186-NA | pHW246-NA | pHW246-NA |
| 7 | pHW187-M | pHW187-M | pHW247-M | pHW247-M |
| 8 | pHW188-NS | pHW188-NS | pHW248-NS | pHW248-NS |

TABLE 1-continued

Plasmid sets used for the recovery of A/WSN/33 (H1N1) and A/Teal/HK/W312/97 (H6N1) Viruses

| virus titer§ | | | | |
|---|---|---|---|---|
| t = 24 h | 0 | $1 \times 10^3$ | 0 | 0 |
| t = 48 h | 0 | $2 \times 10^{6*}$ | 0 | $2 \times 10^3$ |
| t = 72 h | 0 | $2 \times 10^{7*}$ | 0 | $2 \times 10^{5*}$ |

§The numbers represent infectious virus particles per ml of the supenatant of transfected cells as determined 24 h, 48 h and 72 h after transfection.
*Cytopathic effect in the cocultured MDCK cells was observed.

Figure 3B:
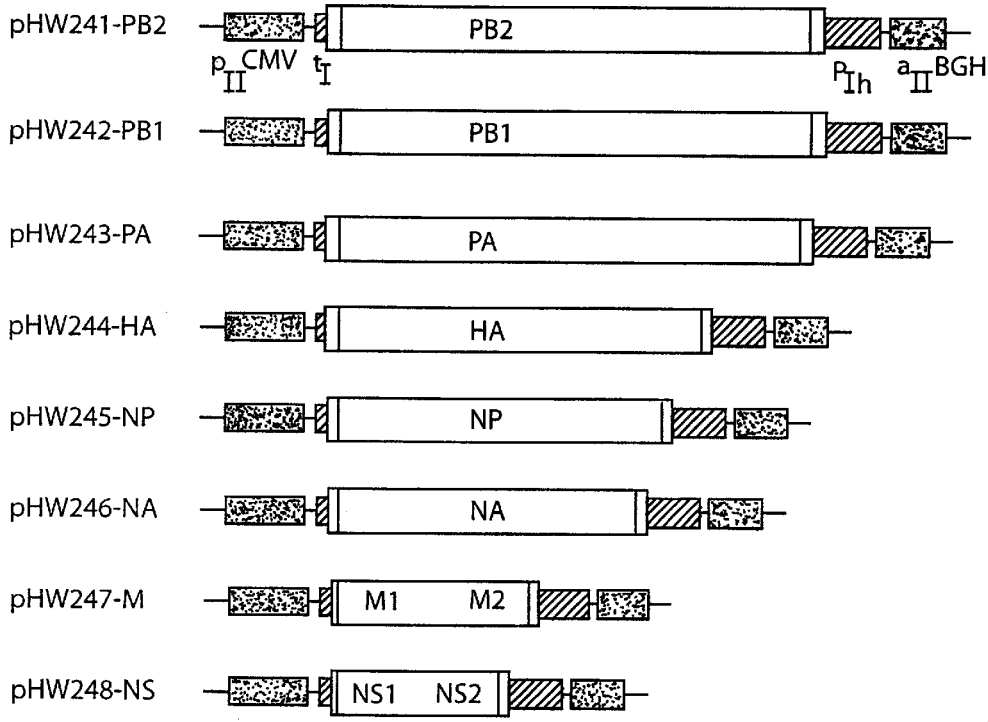
Figure 3B:
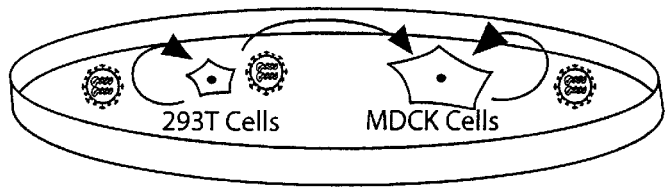
Figure 3B:
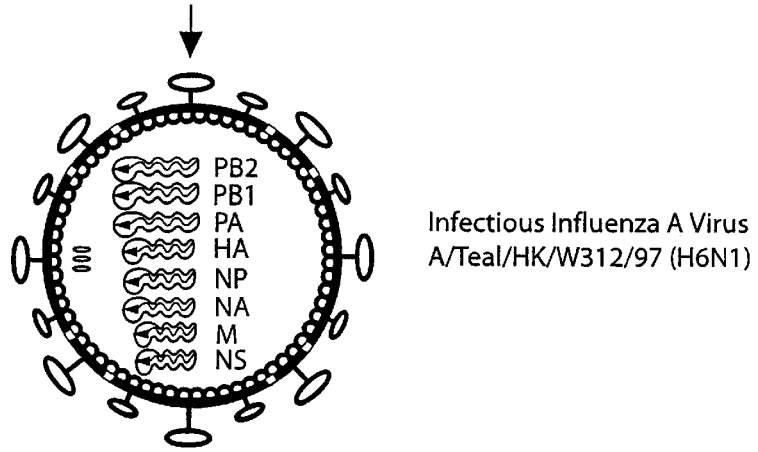

Recovery of A/Teal/HK/W312/97 (H6N1) by cotransfecting eight plasmids. The influenza virus A/WSN/33 (H 1N1), originally derived from the human influenza pandemic strain from 1918 (Goto and Kawaoka, Proc. Acad. Sci. USA 1998, 95: 10224; Reid et al., Proc. Natl. Acad. Sci. USA 1999, 96: 1651), has been passaged in mouse brain and is well adapted for growth in cell culture. To evaluate the efficiency of the eight-plasmid system for the generation of a virus from cloned cDNA that is not already adapted for growth in cell culture, generation of the virus A/Teal/HK/W312/97 (H6N 1) was attempted from cloned cDNA alone. This H6N1 virus was isolated from a dead teal during the H5N1 outbreak in Hong Kong in 1997. Genetic analysis of this virus revealed that it has seven segments with more than 97% nucleotide homology to the pathogenic H5N1 virus strains. RNA was extracted from infected allantoic fluid, and the RT-PCR-amplified cDNAs were inserted into pHW2000; this insertion resulted in eight expression plasmids (FIG. 3). Seventy-two hours after transfection of pHW241-PB2, pHW242-PB1, pHW243-PA, pHW244-HA, pHW245-NP, pHW246-NA, pHW247-M, and pHW248-NS (1 µg each) into cocultured 293T-MDCK cells, a virus-induced cytopathic effect was observed in MDCK cells (Table 1). The virus yield was $2 \times 10^5$ infectious viruses per ml of the supernatant of the transfected cells. As shown in FIG. 4 (A and B, lane 2), the identity of the recovered virus was verified by characterization of the NS segment. These results illustrate that this plasmid system requires the cloning of only eight cDNAs into one plasmid vector and that the transfection of the eight expression plasmids allows the recovery of an influenza A virus with the antigenicity of a virus not already adapted to growth in mammalian cells.

Rescue of reassortment influenza A viruses. The utility of the eight-plasmid system was tested for the generation of reassortment viruses. Because this DNA transfection system does not require any selection system, the recovery of reassortment viruses should be achievable by appropriate combinations of expression plasmids in the transfection reactions. Seven expression plasmids containing the cDNA of A/Teal/HK/W312/97 (H6N 1) were cotransfected with one expression plasmid containing the cDNA of A/WSN/33 (H1N1) (Table 2). High virus yields were obtained for the reassortment viruses containing seven segments of the teal virus and the M segment or NS segment of the WSN virus. Lower virus yields were obtained for the NA and HA-reassortnent viruses (Table 2). Because single reassortment viruses were rescued with the eight-plasmid system, the next step was to determine whether a virus could be rescued with multiple segments derived from one virus. Therefore, four expression plasmids containing the cDNA of the RNP-complex genes of the H6N1 virus (pHW241-PB2, pHW242-PB1, pHW243-PA and pHW245-NP) were transfected together with the plasmids pHW184-HA, pHW186-NA, pHW187-M, and pHW188-NS containing the cDNA of the WSN virus (Table 2). 4×10⁶ viruses were recovered per ml of cell supernatant. As shown in FIG. 4 (lane 10), the amplified NS segment of the quadruple reassortment virus was cleaved by NcoI; thus, the NS segment is derived from the WSN virus. These results show that the eight-plasmid transfection system allows the recovery of single and quadruple reassortment viruses.

expressing the RNP complex proteins (Neumann et al., supra; Fodor et al., J. Virol. 1999, 73: 9679) supports the idea that the generation of infectious influenza A virus is enhanced by providing the HA, NA, M1, M2, and NS2 proteins early after transfection.

The viral replication cycle involves a complex interaction between the viral proteins with each other and with cellular

TABLE 2

Generation of reassortment influenza A viruses between A/Teal/HK/W312 (H6N1) and A/WSN/33 (H1N1) by cotransfecting eight plasmids.

| segment* | HA | NA | M | NS | HA-NA-M-NS |
|---|---|---|---|---|---|
| 1 | pHW241-PB2 | pHW241-PB2 | pHW241-PB2 | pHW241-PB2 | pHW241-PB2 |
| 2 | pHW242-PB1 | pHW242-PB1 | pHW242-PB1 | pHW242-PB1 | pHW242-PB1 |
| 3 | pHW243-PA | pHW243-PA | pHW243-PA | pHW243-PA | pHW243-PA |
| 5 | pHW245-NP | pHW245-NP | pHW245-NP | pHW245-NP | pHW245-NP |
| 4 | pHW184-HA | pHW244-HA | pHW244-HA | pHW244-HA | pHW184-HA |
| 6 | pHW246-NA | pHW186-NA | pHW246-NA | pHW246-NA | pHW186-NA |
| 7 | pHW247-M | pHW247-M | pHW187-M | pHW247-M | pHW187-M |
| 8 | pHW248-NS | pHW248-NS | pHW248-NS | pHW188-NS | pHW188-NS |
| virus titer§ | 2 × 10² | 2 × 10³ | 2 × 10⁵ | 2 × 10⁷ | 4 × 10⁶ |

*plasmids containing the cDNA of A/WSN/33 (H1N1) are shown in bold
§The numbers represent infectious virus particles per ml of supernatant of transfected cells as determined 72 h after transfection.

DISCUSSION

The ability to rescue influenza A virus after transfection of the eight expression plasmids containing the cDNA of A/Teal/HK/W312/97 (H6N1) or A/WSN/33 (H1N1) proves that the pol I-pol II transcription system provides sufficient amounts of vRNA and viral proteins for the formation of infectious influenza A virus. Two types of mRNAs that differ in their noncoding regions are synthesized (FIG. 1). The mRNA type encoding all viral proteins is directly transcribed by pol II. In addition to the influenza virus sequences of the non coding regions (NCR), these mRNAs contain sequences from the pol I promoter and the murine terminator regions. Importantly, the pol I-pol II expression system developed contained only 33 bp of the murine terminator sequences. Previous studies using the reporter genes chloramphenicol acetyltransferase (CAT) and green fluorescent protein (GFP) showed that sequences in the 174-bp terminator region reduced pol II-mediated expression of protein (Hoffmann, E., Ph.D. Thesis 1997, Justus Liebig University, Giessen, Germany). A second mRNA type is generated after the initiation of the viral replication and transcription process (FIG. 2). This mRNA is synthesized by the viral polymerase proteins and contains a 5 cap structure derived from cellular RNAs by cap snatching preceding the influenza virus noncoding sequences. The structural proteins translated from both mRNAs associate with the RNP complexes to form new virus particles. After the budding of transfectant viruses, the generated virus particles can then replicate in the 293T cells and in the cocultured MDCK cells.

Unlike the approaches discussed in the Background of the Invention, supra, the method of the instant invention deploys the eight cDNAs in eight plasmids that contained 225 bp of the pol I promoter sequences and 33 bp of the terminator sequences. In the pol I-pol II system, all 10 viral proteins are expressed from a truncated immediate-early promoter of the human cytomegalovirus. The fact that the expression of all structural proteins with the 17-plasmid system (Neumann et al., Proc. Natl. Acad. Sci. USA 1999, 96: 9345) and with the 8-plasmid system (this study) resulted in a higher efficiency of virus recovery than did cotransfection of plasmids factors (Ludwig et al., Virol. Immunol. 1999, 12: 175). Thus, for the generation of infectious virus, the plasmid-driven synthesis of viral molecules should provide optimal concentrations of viral proteins for the initiation of the replication cycle and for the formation of virus-like particles. Although the eight-plasmid system proved to be efficient, it might be possible to further increase the production of virus. It was shown that the ratio of transfected plasmids expressing the RNP complex proteins and the expression of the M1 protein influences the transcriptase activity (Pleschka et al., J. Virol. 1996, 70: 4188; Perez and Donis, Virology 1998, 249: 52). The efficiency of the formation of virus-like particles also depends on the concentration of structural viral proteins (Mena et al., J. Virol. 1996, 70: 5016; Gomez-Puertas et al., J. Gen. Virol., 1999, 80: 1635; Neumann et al., J. Virol. 2000, 74: 547). The efficiency of the generation of infectious virus with the pol I-pol II system might therefore be further increased by varying the plasmid concentrations used in the transfection reaction or by using expression plasmids with different pol II promoters. Because the splicing efficiency mediated by cellular factors influences the ability of influenza A virus to replicate (Lau and Scholtissek, Virology 1995, 212: 225), the use of cell lines other than 293T may increase the virus yield for certain influenza A strains. The high virus yield of the quadruple reassortment (Table 2) is consistent with the finding that the rapid replication of A/WSN/33 (H1N1) in cultured cells is mediated by the HA, NA, and M segments (Goto and Kawaoka, Proc. Nat). Acad. Sci. USA 1998, 95: 10224; Schulman and Palese, J. Virol. 1977, 24: 170; Yesuda et al., J. Virol. 1994, 68: 8141).

The generation of viable reassortants (Table 2) between the avian H6N1 virus and the human H1N1 virus indicates that this H6N1 virus can acquire gene segments from a distantly related virus. Genetic analysis suggested that the pathogenic H5N1 viruses were generated by reassortment (Xu et al., Virology 1999, 261: 15). H5N1-like gene segments are found in the H6N1 and H9N2 subtypes (Guan et al., Proc. Natl. Acad. Sci. USA 1999, 96: 9363), a finding indicating that these viruses may have been precursors of the pathogenic H5N1 viruses. Reassortment events that could create new pathogenic influenza viruses are likely to occur in the future. However, the ability to generate and manipulate these viruses by the simplified method developed in this study will help researchers better understand the biological properties of these new viruses and develop efficient vaccines to protect a population against them. The length of the time period between the emergence of a new pathogenic strain and the preparation of a vaccine is a crucial variable in the effectiveness of a vaccination program. The ability to generate viruses by cloning only eight plasmids reduces the time needed for the generation of potential vaccine candidates and improves existing reverse-genetics systems by simplifying virus creation and reducing the overall cost of production of a vaccine.

The concept of introducing viral cDNA between a pol I promoter and a pol II promoter into eukaryotic cells for the recovery of virus is also applicable for the generation of other members of the family Orthomyxoviridae. For influenza B virus, this strategy would require the construction and cotransfection of eight plasmids; for influenza C, seven; and for Thogotovirus, six. The in vivo transcription of 5'-capped mRNA as well as vRNA from the same cDNA template may also simplify plasmid-based systems for other RNA viruses or even facilitate the establishment of pol I-pol II systems for viruses from other families (e.g. Arenaviridae, Bunyaviridae).

EXAMPLE 3

RNA Pol I/Pol II System for the Generation of Influenza B Virus Entirely from Cloned cDNA Influenza A and B viruses each contain eight segments of single stranded RNA with negative polarity (for review see Lamb and Krug, "Orthomyxoviridae: The viruses and their replication"; in Fields (Ed.), *Virology*; p 1353–1395). Unlike influenza A, the eight segments of influenza B encode 11 proteins. The three largest genes code for the components of the RNA polymerase, PB1, PB2 and PA; segment 4 encodes the haemagglutinin. Segment 5 encodes the nucleoprotein, the major structural component associated with viral RNA, segment 6 encodes the neuramimidase (NA) and the NB protein. Both proteins, NB and NA, are translated from overlapping reading frames of a biscistronic mRNA. Segment 7 of influenza B also encodes two proteins: BM1 and BM2. The smallest segment encodes two products: NS1 is translated from the full length RNA, while NS2 is translated from a spliced mRNA.

Construction of expression plasmids containing the cDNA of influenza B involves the same strategy as described for the generation of the influenza A virus A/teal/HK/W312/97 (H6N 1). First RNA is isolated from virus particles obtained from infected allantoic fluid, e.g., B/Lee/40. Based on the conserved sequences of the noncoding region, primers for the RT-PCR are prepared and used for the synthesis of cDNA. At the 5'-end those primers contain sequences for the restriction endonucleases BsmBI or BsaI. Digestion of the PCR products with BsmBI or BsaI allows the insertion into the cloning vector pHW2000 (or pHW11) linearized with BsmBI. To ensure that the cDNAs in the plasmids do not have unwanted mutations due to errors made by the polymerase during PCR, the constructs have to be sequenced.

Co-transfection of cocultured 293T-MDCK cells (or COS-1-MDCK) cells and the addition of trypsin results in the generation of infectious influenza B virus. The supernatants of transfected cells are then passaged onto new MDCK cells. The resultant virus titer can be determined by standard methods, e.g., the HA assay and plaque assay. RT-PCR performed with specific primers for each gene segment allows the amplification of the RNA from the recombinant influenza B virus. Sequencing of the products confirms that the generated virus is indeed the desired influenza B virus.

EXAMPLE 4

Eight-plasmid Rescue System for Master Strain Influenza A Virus

To determine the commercial utility of this plasmid-based system for the production of vaccines, we generated the masterstrain A/PR/8/34 (H 1N1), currently used for production of inactivated vaccine, entirely from cloned cDNAs as described in Example 2. The virus yield as determined by HA-assay after passage of the recombinant virus into eggs was as high as the virus yield of the parental wildtype virus. These results prove that the generated recombinant virus has the same growth properties as the parental egg grown virus and indicate that the eight-plasmid transfection method has the potential to improve currently used methods for the production of vaccine viruses.

Materials and Methods

Viruses and Transfection. The Influenza virus A/PR/8/34 (H1N1) was obtained from the repository of St. Jude Childrens's Research Hospital and propagated in 10-day-old embryonated chicken eggs. Madin-Darby canine kidney (MDCK) cells were maintained in MEM containing 10% FBS. 293T human embryonic kidney cells and Vero cells were cultured in Opti-MEM I (Life Technologies, Gaithersburg, Md.) containing 5% fetal bovine serum (FBS). For the transfection experiments, six-well tissue culture plates were used. The cocultured MDCK and 293T cells ($0.21 \times 10^6$ each of cells per well) were used for the transfection experiments. TransIT LT-1 (Panvera, Madison, Wis.) was used according to the manufacturer's instructions to transfect the cells. Briefly, 2 $\mu$l of TransIT LT-1 per 1 $\mu$g of DNA was mixed, incubated at room temperature for 45 min, and added to the cells. Six hours later, the DNA-transfection mixture was replaced by Opti-MEM I. Twenty four hours after transfection, 1 ml of Opti-MEM I containing TPCK-trypsin was added to the cells; this addition resulted in a final concentration of TPCK-trypsin of 0.5 $\mu$g/ml in the cell supernatant. The virus titer was determined by passage of the cell supernatant on MDCK cells by plaque assay.

RT-PCR and Construction of Plasmids. Viral RNA was extracted from 200 $\mu$l of virus containing allantoic fluid of embryonated egg using Qiagen RNeasy Kit. Two-step RT-PCR was employed to amplify each of the viral gene segments. Briefly, the RNA was transcribed into cDNA using AMV reverse transcriptase (Roche Diagnostics, Germany) according to the protocol provided and then the cDNA was amplified using Expand High Fidelity PCR system (Roche Diagnostics, Germany). The amplification program started with 1 cycle at 94° C. for 2 min; followed by 30 cycles at 94° C. for 20 seconds, 54° C. for 30 seconds, 72° C. for 3 min; the program ended with one cycle at 72° C. for 5 minutes. The primers used contained either sequences for BsaI or BsmBI to allow the precise insertion of the digested PCR-fragments into the cloning vector pHW2000 (see Example 2).

For cloning of the HA, NP, NA, M, NS genes the PCR-fragments were digested with BsmBI or BsaI and ligated into the cloning vector pHW2000. For cloning of the P-genes two (PB2, PA) or three (PB1) fragments were isolated, digested and ligated into pHW2000-BsmBI. To ensure that the genes were free of unwanted mutations, the PCR-derived fragments were sequenced. The eight plasmids containing the full length cDNA of A/PR/8/34 (H1N1) were designated pHW191-PB2, pHW192-PB1, pHW193-PA, pHW194-HA, pHW195-NP, pHW196-NA, pHW197-M, and pHW198-NS. The Center for Biotechnology at St. Jude Children's Research Hospital determined the sequence of template DNA by using rhodamine or dRhodamine dye-terminator cycle sequencing ready reaction kits with Ampli-Taq® DNA polymerase FS (Perkin-Elmer, Applied Biosystems, Inc. [PE/ABI], Foster City, Calif.) and synthetic oligonucleotides. Samples were subjected to electrophoresis, detection, and analysis on PE/ABI model 373, model 373 Stretch, or model 377 DNA sequencers.

RESULTS

To allow intracellular synthesis of virus-like vRNAs and mRNAs, we have established the RNA pol I-pol II expression system (see Example 2). In this system viral cDNA is inserted between the human RNA polymerase I (pol I) promoter and a terminator sequences. This entire pol I transcription unit is flanked by an RNA polymerase II (pol II) promoter and a poly(A) site. The orientation of the two transcription units allows the synthesis of negative-sense viral RNA and positive-sense mRNA from one viral cDNA template. This pol I-pol II system starts with the initiation of transcription of the two cellular RNA polymerase enzymes from their own promoters, presumably in different compartments of the nucleus (see FIG. 1). Transfection of eight plasmids into 293T cells results in the interaction of all molecules derived from the cellular and viral transcription and translation machinery, ultimately generating infectious influenza A virus. This system proved to be very efficient for the formation of the influenza viruses A/WSN/33 (H1N1) and A/Teal/HK/W312/97 (H6N 1) (Example 2).

Since the current master strain for production of inactivated influenza vaccine is A/PR/8/34 (H1N1), we attempted to generate this virus entirely from cloned cDNA. The cDNAs representing the eight RNA-segments were inserted into the vector pHW2000. The resultant plasmids (pHW191-PB2, pHW192-PB1, pHW193-PA, pHW194-HA, pHW195-NP, pHW196-NA, pHW197-M, and pHW198-NS) were transfected into cocultured 293T-MDCK or Vero-MDCK cells. Seventy-two hours after transfection the virus titer was determined by titration in MDCK cells. The supernatant of cocultured Vero-MDCK cells contained $1\times10^4$ pfu and the supernatant of cocultured 293T-MDCK cells contained $2\times10^6$ pfu per ml. The higher yield in 293T-MDCK cells is most likely caused by the higher transfection efficiency of 293T cells compared to Vero cells. These results show that the eight-plasmid system allows the generation of A/PR/8/34 (H1N1) from cloned cDNA.

To compare the growth between the wildtype virus and the generated recombinant virus, embryonated hen's eggs were inoculated with wildtype virus or recombinant virus. The allantoic fluid was harvested 48 hours after infection. The virus yield was determined by HA-assay. Although the HA-titers differed between individual eggs, we found that both viruses had HA-titers between 5120 and 10240 hemagglutination units, indicating that both viruses are high yielding isolates. Thus, the recombinant virus that was generated by DNA transfection has the same robust culture phenotype as the parental isolate.

DISCUSSION

The eight-plasmid system of the invention avoids the use of separate plasmids for protein expression (see Background of the Invention), thus simplifying the method of generation of influenza A virus entirely from cloned cDNA. The production of vaccines involves the generation of a virus that is used as virus seed for the production of a vaccine virus either in eggs or in cell culture. Efficacy of a vaccination program depends on selecting a subtype that matches the circulating pathogenic strains closely to stimulate a high specific antibody titer in the vaccinated population, resulting in efficient protection. The six A/PR/8/34 master plasmids (pHW191-PB2, pHW192-PB1, pHW193-PA, pHW195-NP, pHW197-M, and pHW198-NS) encoding the internal influenza A genes can now be used in cotransfection with plasmids encoding the glycoproteins HA and NA of a currently circulating strain. The ability to manipulate each gene segment will also allow us to evaluate which gene segment(s) are important for high yield growth of the reassortant viruses in eggs as well as in cell culture.

The fact that we were able to generate two laboratory influenza virus strains (A/WSN/33 (H1N1) and A/PR/8/34 (H1N1)) and one field isolate (A/Teal/HK/W312/97 (H6N1)) by cotransfecting only eight plasmids suggests that this system is applicable for the development of live attenuated influenza vaccines. Live attenuated influenza virus vaccines administered intranasally induce local, mucosal, cell-mediated and humoral immunity. Cold-adapted (ca) reassortant (CR) viruses containing the six internal genes of live, attenuated influenza A/Ann Arbor/6/60 (H2N2) and the haemagglutinin (HA) and neuramimidase (NA) of contemporary wild-type influenza viruses appear to be reliably attenuated. This vaccine has been shown to be efficacious in children and young adults (Keitel & Piedra *In Textbook of Influenza*, Nicholson et al., eds. 1998, 373–390. However, it may be too attenuated to stimulate an ideal immune response in elderly people, the major group of the 20,000 to 40,000 individuals in the USA dying each year as a result of influenza infection. The contribution of each segment to the attenuated phenotype is still not well defined (Keitel & Piedra, supra). This information can be acquired only by the sequential introduction of specific, defined attenuating mutations into a virus. Since a detailed analysis requires the testing of a large number of manipulated viruses, the construction and transfection of only eight plasmids simplifies this task and reduces the time and cost to achieve this goal.

EXAMPLE 5

Unidirectional RNA Polymerase I-Polymerase II Transcription System for the Generation of Influenza A Virus from Eight Plasmids The previously Examples describe a system for the generation of influenza A virus by cotransfecting only eight plasmids from which negative-sense vRNA and positive-sense mRNA are expressed (this work was subsequently published; see Hoffmann et al., 2000, Proceedings of the National Academy of Sciences, USA 97, 6108–6113). This Example describes the establishment of a different transcription system for the expression of virus-like RNAs, allowing the intracellular synthesis of noncapped positive-sense cRNA and 5'-capped mRNA from one template. Cotransfection of eight RNA pol I-pol II tandem promoter plasmids containing the cDNA of A/WSN/33 (H1N1) resulted in the generation of infectious influenza A virus, albeit with lower virus yield than the bidirectional system. Our approach of producing either vRNA and mRNA or cRNA and mRNA intracellularly from a minimum set of plasmids is useful for the establishment or optimization of reverse genetics systems of other RNA viruses.

The results reported in this Example were published (see Hoffmann and Webster, J. Gen. Virol. 2000, 81: 2843).

Figure 5:
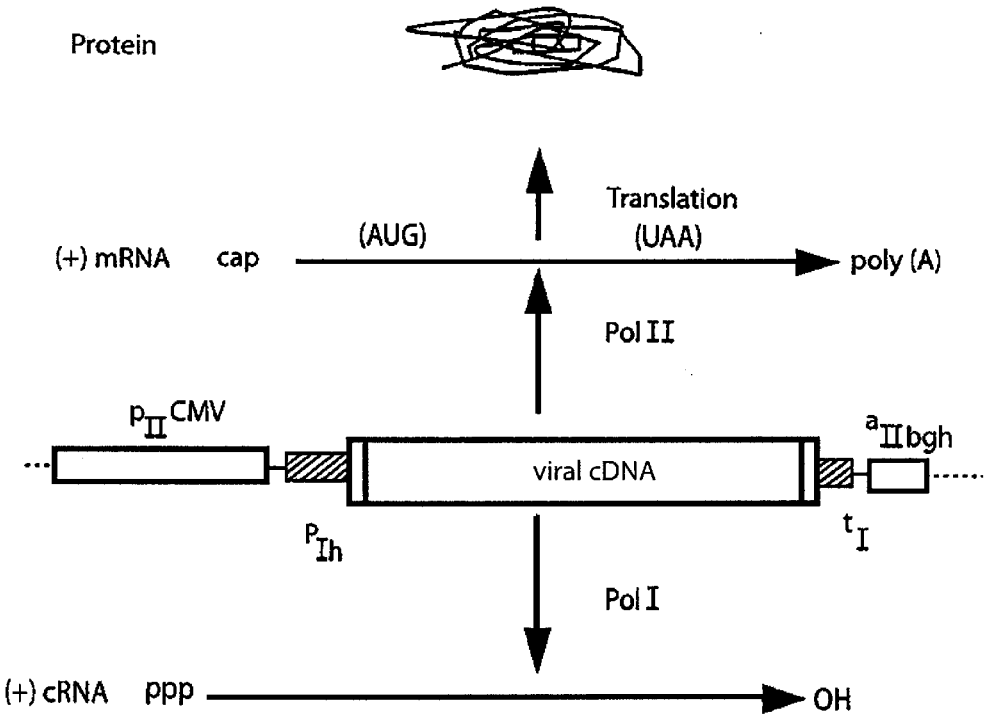
FIG. 5. Unidirectional RNA pol I-pol II transcription system. In the unidirectional pol I-pol II transcription system, viral cDNA is inserted in the positive-sense orientation between a human pol I promoter ($p_{Ih}$) and terminator sequence ($t_I$). This entire pol I transcription unit is flanked by a pol II promoter ($p_{II}CMV$: immediate early promoter of the human cytomegalovirus) and the polyadenylation site of the gene encoding bovine growth hormone ($a_{IIbgh}$). After transfection, two types of RNA transcripts are expected to be synthesized. Positive-sense cRNA with a triphosphate group at its 5' end synthesized by pol I, and positive-sense mRNA synthesized by pol II with a 5'-cap structure and a poly(A) tail at its 3' end. Both elements of the mRNA are required for efficient translation.
Figure 6:
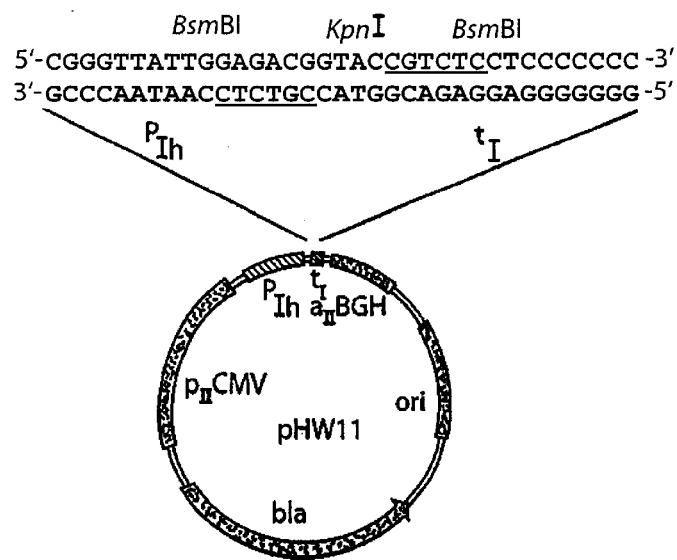
FIG. 6. The cloning vector pHW11 with a pol I and a pol II promoter arranged in tandem. The plasmid contains the 225-bp human RNA pol I promoter ($p_{Ih}$) and the 33-bp murine terminator ($t_I$). The pol I promoter and terminator sequences are flanked by the RNA polymerase II promoter ($p_{II}CMV$) of the human cytomegalovirus and the polyadenylation signal (aIIBGH) of the gene encoding bovine growth hormone. For insertion of viral cDNA between the pol I promoter and terminator, two BsmBI restriction sites (indicated by underlining) were introduced. Digestion of the vector with BsmBI created a vector fragment with sticky but noncomplementary protruding ends. The design of this vector allows the precise fusion of viral cDNA in the positive-sense orientation with respect to the pol I promoter and terminator sequence. For propagation in E. coli, the plasmid has an origin of replication (ori), and for selection in ampicillin-containing medium, the plasmid contains a beta-lactamase gene (bla).
Figure 7A:
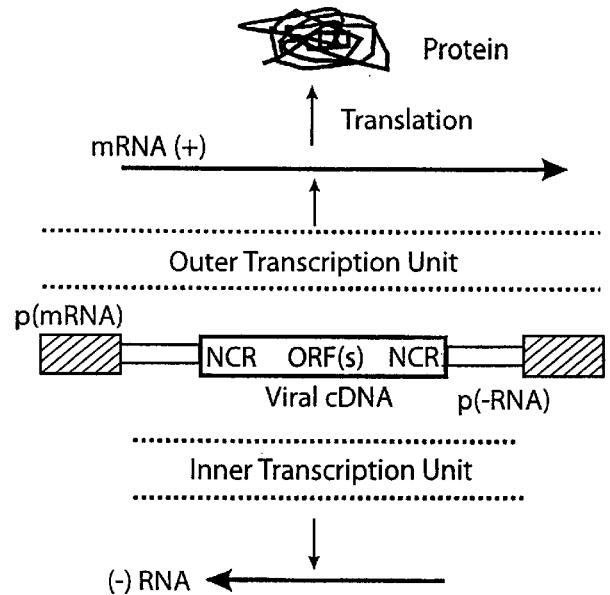
FIGS. 7A and 7B. Dual promoter system for the generation of infectious RNA viruses. Since RNA viruses function as cellular parasites they must optimize strategies for using host cells for expression of their genetic information. All RNA viruses must synthesize mRNAs which are capable of being translated into proteins. Generally, the synthesized proteins are required for replication, transcription and producing new progeny virus particles. For efficient replication of the genomic RNAs, RNA-transcripts with exact 5' and 3' ends must be made.
Figure 7B:
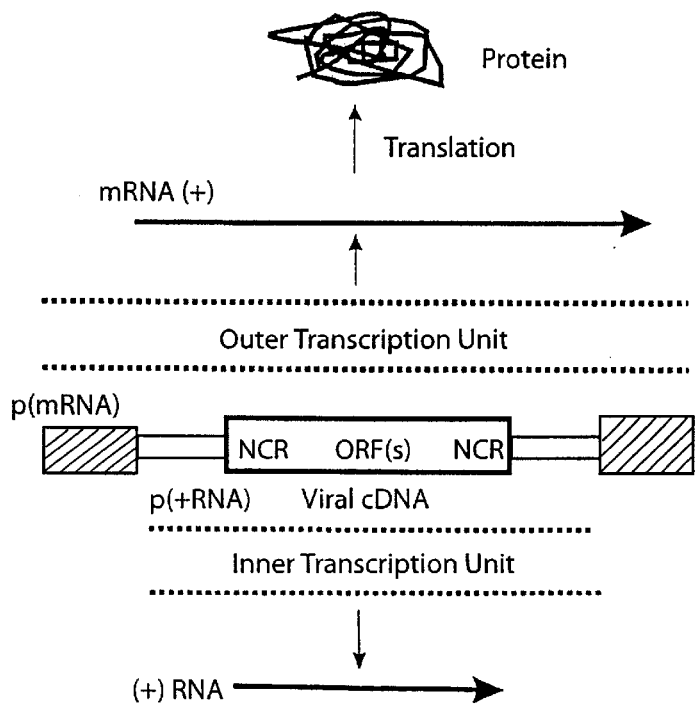

For the generation of negative-sense RNA virus, either negative-sense vRNA or positive-sense cRNA can serve as a template. To reduce the number of plasmids needed for the recovery of virus, we reasoned that it might be possible for cellular RNA pol I and pol II to synthesize cRNA and mRNA from one template. Therefore we attempted to develop a unidirectional pol I-pol II transcription system (FIG. 5). Viral cDNA is inserted in the positive-sense orientation between an RNA pol I promoter and a terminator sequence. This whole pol I transcription unit is inserted in the positive-sense orientation between an RNA pol II promoter and a polyadenylation site (FIG. 5). Unlike, the negative-sense vRNA and positive-sense mRNA generated in our bidirectional transcription system (FIG. 1), two types of positive-sense RNAs were expected to be synthesized. From the pol II promoter, an mRNA with a 5'-cap structure should be transcribed in the nucleoplasm. This transcript should be translated into protein. In the nucleolus, cellular pol I is expected to synthesize full-length, positive-sense influenza virus cRNA with a triphosphate group at the 5' end (FIG. 5). A cloning vector, pHW11, that can be used for insertion of arbitrary cDNA fragments was constructed (FIG. 6). This plasmid contains the pol II promoter (immediate early promoter of the human cytomegalovirus) and the human pol I promoter that are upstream of a pol I terminator sequence and a poly(A) site.

To test whether infectious influenza A virus can be generated by synthesizing cRNA and mRNA from a single template, we constructed eight plasmids. The plasmids pHW171-PB2, pHW172-PB1, pHW173-PA, pHW174-HA, pHW175-NP, pHW176-NA, pHW177-M, and pHW178-NS contain the cDNAs representing the eight gene segments of influenza A strain A/WSN/33 (H1N1). All of these cDNAs are in the positive-sense orientation with regard to the pol I and pol II promoters. The eight plasmids (1 μg of each plasmid) were transfected into 293T or COS-1 cells with or without co-culturing with MDCK cells as described in Example 2.

The virus yield in the supernatant of transfected cells at different times was determined by plaque assay after passage on MDCK cells. Forty-eight hours after transfection 2–5× $10^3$ infectious virions were produced (Table 3). Seventy two hours after transfection the supernatant contained $4 \times 10^4$ pfu/ml after transfection of 293T or $2 \times 10^4$ pfu/ml after transfection of COS-1 cells. The virus yield after 72 h could be increased by co-culturing 293T cells or COS-1 cells with MDCK cells (Table 3).

The generation of virus proves that after transfection of the eight plasmids, RNA pol I synthesized the eight noncapped, positive-sense cRNAs. The four viral polymerase proteins translated from cellular RNA pol II-synthesized transcripts bound to the naked virus-like cRNAs to form cRNPs. The polymerase subunit PB1 is important for the recognition of the terminal structure and binding of the virus-like cRNAs (Gonzalez & Ortin EMBO J. 1999, 18: 3767; Gonzalez & Ortin, J. Virol. 1999, 73: 631; and 1999b; Li et al., EMBO J. 1998, 17: 5844). The interaction with other polymerase proteins started the replication-transcription cycle, which resulted in the synthesis of vRNPs and viral mRNAs (Toyoda et al., J. Gen. Virol. 1996, 77: 2149; Gonzalez et al., Nucl. Acids Res. 1996, 29: 4456). In the pol I-pol II transcription system, two different mRNA types are synthesized. One is directly transcribed from the plasmid-DNA by RNA pol II and contains the 225-nt pol I promoter sequence in the 5' end and the pol I terminator sequence in the 3' end. Another mRNA is synthesized by viral polymerase complex proteins that use the vRNA as template. The 5' cap structure of this mRNA is acquired by the cap-snatching mechanism in which the polymerase subunit PB2 takes the cap from cellular RNAs (Ulmanen et al., Proc. Natl. Acad. Sci. USA 1981, 21: 3607). Although both mRNA types differ in their 5' and 3' noncoding regions, they contain the same open reading frames for all viral proteins. The translated structural proteins together with the vRNPs assemble to create infectious influenza A virus.

TABLE 3

Plasmid sets used for the production of A/WSN/33 (H1N1).

| Virus gene segment | Plasmids* | | | | | | | |
|---|---|---|---|---|---|---|---|---|
| | unidirectional system | | | | bidirectional system | | | |
| 1 | pHW171-PB2 | pHW171-PB2 | pHW171-PB2 | pHW171-PB2 | pHW181-PB2 | pHW181-PB2 | pHW181-PB2 | pHW181-PB2 |
| 2 | pHW172-PB1 | pHW172-PB1 | pHW172-PB1 | pHW172-PB1 | pHW182-PB1 | pHW182-PB1 | pHW182-PB1 | pHW182-PB1 |
| 3 | pHW173-PA | pHW173-PA | pHW173-PA | pHW173-PA | pHW183-PA | pHW183-PA | pHW183-PA | pHW183-PA |
| 4 | pHW174-HA | pHW174-HA | pHW174-HA | pHW174-HA | pHW184-HA | pHW184-HA | pHW184-HA | pHW184-HA |
| 5 | pHW175-NP | pHW175-NP | pHW175-NP | pHW175-NP | pHW185-NP | pHW185-NP | pHW185-NP | pHW185-NP |
| 6 | pHW176-NA | pHW176-NA | pHW176-NA | pHW176-NA | pHW186-NA | pHW186-NA | pHW186-NA | pHW186-NA |
| 7 | pHW177-M | pHW177-M | pHW177-M | pHW177-M | pHW187-M | pHW187-M | pHW187-M | pHW187-M |
| 8 | pHV178-NS | pHW178-NS | pHW178-NS | pHW178-NS | pHW188-NS | pHW188-NS | pHW188-NS | pHW188-NS |
| Transfected cells[#] | 293T | 293T +MDCK | COS-1 | COS-1 +MDCK | 293T | 293T +MDCK | COS-1 | COS-1 +MDCK |
| Transcripts[†] | cRNA and mRNA | | | | vRNA and mRNA | | | |
| Virus titer (pfu/ml)[§] | | | | | | | | |
| t = 24 h | 0 | 0 | 0 | 0 | $5 \times 10^2$ | $4 \times 10^2$ | $1 \times 10^3$ | $1 \times 10^3$ |
| t = 48 h | $4 \times 10^3$ | $5 \times 10^3$ | $2 \times 10^3$ | $5 \times 10^3$ | $8 \times 10^6$ | $1 \times 10^7$ | $6 \times 10^6$ | $1 \times 10^7$ |
| t = 72 h | $4 \times 10^4$ | $2 \times 10^5$ | $2 \times 10^4$ | $4 \times 10^5$ | $1 \times 10^7$ | $2 \times 10^8$ | $1 \times 10^7$ | $3 \times 10^8$ |

*The plasmids with the unidirectional transcription units and the plasmids with bidirectional transcription units (FIG. 1) contain cDNAs representing the eight gene segments of A/WSN/33 (H1N1).
[#]293T or COS-1 cells were transfected either without or with co-cultured MDCK cells.
[†]RNA transcripts synthesized by pol I or pol II.
[§]Virus titer of the supernatant was determined at the indicated times (24 h, 48 h, 72 h) after transfection by plaque assay on MDCK cells.

Although the generation of WSN-virus from cells transfected with eight tandem-promoter plasmids proved to be very reliable, the virus yield by this cRNA-mRNA approach was lower than that of the bidirectional system that produces vRNA and mRNA transcripts (Table 3). Seventy-two hours after 293T or COS-1 cells had been transfected with the eight plasmids containing the bidirectional pol I-pol II transcription system (FIG. 1; Example 2; see Hoffmann et al., Proc. Natl. Acad. Sci. USA 2000, 97: 6108; pHW181-PB2, pHW182-PB1, pHW183-PA, pHW184-HA, pHW185-NP, pHW186-NA, pHW187-M, and pHW188-NS), the virus titer was $1 \times 10^7$ pfu/ml (Table 3). Twenty four hours after transfection of COS-1 or 293T cells $0.4-1 \times 10^3$ pfu/ml were found in the supernatant. These data show that the eight plasmid bidirectional system has the same efficiency for virus generation with similar kinetics as the more complicated and cumbersome multi plasmid system requiring cotransfection of 12 or 17 plasmids (Neumann et al., Proc. Natl. Acad. Sci. USA 1999, 96: 9345).

No infectious virus was found 24 h posttransfection with eight tandem promoter plasmids (Table 3). These results suggest that the differences in virus yields between the vRNA-mRNA and cRNA-mRNA approaches are due to the different polarities of the primary pol I transcripts. The bidirectional system starts with the intracellular synthesis of vRNA, a situation resembling the natural influenza A infection in which vRNPs are transported to the nucleus and vRNAs initially serve as templates for mRNA and cRNA synthesis. In the unidirectional system, cRNPs are the first replication-competent units that are produced. To produce mRNAs, the cRNAs have to be replicated into vRNAs, and the vRNPs are ultimately packaged into progeny virus particles (Hsu et al., J. Gen. Virol. 1987, 77: 2575). Because of the additional reactions required for the generation of vRNPs from cRNPs, the formation of virus in the unidirectional system occurs at a later time than does virus formation by the bidirectional system.

Other possible reasons for the differences in virus yields of the two systems are that sequence elements in the cDNA decrease the efficiency of transcription by terminating transcription, or sequences in the RNA transcripts reduce the steady-state level of the pol I or pol II transcripts. A lower concentration of only one of the eight virus-like cRNAs or mRNAs reduces the overall efficiency of this system because all vRNPs and structural proteins have to be synthesized in concentrations that are optimal for virus replication and virus assembly.

The high efficiency of the eight-plasmid system for the generation of influenza A virus indicates that this system applies to other orthomyxoviruses, e.g., influenza B virus, influenza C virus, and Thogotovirus. The results in this study suggest that the vRNA-mRNA system will be the most efficient way for generating these viruses entirely from plasmids. The present invention permits establishment of pol I based systems for the generation of RNA viruses other than members of the family Orthomyxoviridae, e.g., members of Paramyxoviridae, Arenaviridae or Bunyaviridae (Roberts, A. & Rose, J. K., Virology 1998, 247: 1–6; Bridgen & Elliot, Proc. Natl. Acad. Sci. USA 1996, 93: 15400; Lee et al., J. Virol. 2000, 74: 3470). Unlike orthomyxoviruses, most RNA viruses replicate in the cytoplasm of infected cells. During their evolution the RNAs of these viruses have not been subjected to selection pressures found in the nucleus, e.g. splicing. Generally, reverse genetics systems for nonsegmented negative strand RNA viruses are based on the intracellular transcription from a T7 promoter as pioneered by Conzelmann and colleages for the rescue of rabiesvirus (Schnell et al., EMBO J. 1994, 13: 4195). The expression of virus-like RNAs is driven by T7 RNA polymerase provided either by infection with a recombinant vaccinia virus or by using cell lines constitutively expressing T7 RNA polymerase. Unlike pol I transcription which, occurs in the nucleus, transcription by T7 RNA polymerase takes place in the cytoplasm. Use of the pol I transcription system for cytoplasmic RNA viruses would require that the RNA transcripts have to be transported out of the nucleus. That indeed pol I transcripts are transported out of the nucleus is supported by the detection of protein production in cells containing pol I transcripts that had an internal ribosomal entry site inserted into its 5' noncoding region (Palmer et al., Nucl. Acids. Res. 1993, 21: 3451). Because information is limited about the sequences crucial for export or retention of pol I transcripts, synthesis of negative-sense or positive-sense RNAs may result in different efficiencies of nuclear export. In addition, the export of a large pol II-generated coronavirus-like transcript (having greater than 30,000 nts) from the nucleus (Almazán et al., Proc. Natl. Acad. Sci. USA 2000, 97: 5516) indicates that specific RNA sequences rather than the length of a transcript may be crucial for export. The pol I-pol II cloning vectors that we have developed and the efficient cloning method based on the use of type IIs restriction endonucleases will allow positive and negative-sense RNA synthesized in the nucleus for the generation of cytoplasmic RNA viruses at reasonable costs and within a reasonable period of time.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

All patents, patent applications, publications, and other materials cited herein are hereby incorporated herein reference in their entireties.

What is claimed:

1. A composition which generates infectious influenza viruses from cloned viral cDNA comprising a set of plasmids wherein each plasmid comprises one viral genomic segment, and wherein viral cDNA corresponding to the viral genomic segment is inserted between an RNA polymerase I (pol I) promoter and a regulatory element for the synthesis of vRNA or cRNA with an exact 3' end, which results in expression of vRNA or cRNA, which are in turn inserted between an RNA polymerase II (pol II) promoter and a polyadenylation signal, which results in expression of viral mRNA and a corresponding viral protein, wherein the expression of the full set of vRNAs or cRNAs and viral proteins results in assembly of an infectious influenza virus.

2. The composition of claim 1, wherein the regulatory element for the synthesis of vRNA or cRNA with an exact 3' end is an RNA polymerase I (pol I) terminator sequence.

3. The composition of claim 1, wherein the regulatory element for the synthesis of vRNA or cRNA with an exact 3' end is a ribozyme sequence.

4. The composition of claim 2, wherein the pol I promoter is proximal to the polyadenylation signal and the pol I terminator sequence is proximal to the pol II promoter.

5. The composition of claim 2, wherein the pol I promoter is proximal to the pol II promoter and the pol I terminator sequence is proximal to the polyadenylation signal.

6. The composition of claim 1, wherein the influenza virus is an influenza A virus.

7. The composition of claim 1, wherein the influenza virus is an influenza B virus.

8. The composition of claim 6, wherein the viral genomic segment (i) encodes a protein selected from the group consisting of a viral polymerase complex protein, M protein and NS protein; and (ii) is derived from a strain well adapted to grow in cell culture or from an attenuated strain, or both.

9. The composition of claim 6, wherein the viral genomic segment comprises hemagglutinin (HA) gene, or neuramimidase (NA) gene, or both; wherein said genes are from a pathogenic influenza virus.

10. The composition of claim 6 wherein said composition comprises one or more plasmids having a map selected from the group consisting of pHW241-PB2, pHW242-PB1, pHW243-PA, pHW244-HA, pHW245-NP, pHW246-NA, pHW247-M, and pHW248-NS.

11. The composition of claim 6, wherein said composition comprises one or more plasmids having a map selected from the group consisting of pHW181-PB2, pHW182-PB1, pHW183-PA, pHW184-HA, pHW185-NP, pHW186-NA, pHW187-M, and pHW188-NS.

12. A host cell comprising the composition of claim 1.

13. A host cell comprising the composition of claim 7.

14. A host cell comprising the composition of claim 6.

15. A host cell comprising the composition of claim 9.

16. A method for producing an infectious influenza virus virion, which method comprises culturing the host cell of claim 12 under conditions that permit production of viral proteins and vRNA or cRNA, whereby an infectious influenza virus is produced.

17. A method for producing a pathogenic influenza virion, which method comprises culturing the host cell of claim 15 under conditions that permit production of viral proteins and vRNA or cRNA, whereby a pathogenic infectious influenza virus is produced.

18. A method for generating an attenuated influenza virus, which method comprises:

(a) mutating one or more viral genes in the composition of claim 1; and (b) determining whether infectious influenza viruses produced by the composition upon introduction into a suitable host cell are attenuated.

* * * * *

SEQUENCE LISTING

<160> NUMBER OF SEQ ID NOS: 19

<210> SEQ ID NO 1
<211> LENGTH: 19
<212> TYPE: DNA
<213> ORGANISM: Artificial Sequence
<220> FEATURE:

-continued

<223> OTHER INFORMATION: Seq-PB#1 primer

<400> SEQUENCE: 1
aggatgggat tcctcaagg                                                19

<210> SEQ ID NO 2
<211> LENGTH: 20
<212> TYPE: DNA
<213> ORGANISM: Artificial Sequence
<220> FEATURE:
<223> OTHER INFORMATION: Seq-PB1#2 primer

<400> SEQUENCE: 2
gctatggttt ccagagcccg                                               20

<210> SEQ ID NO 3
<211> LENGTH: 28
<212> TYPE: DNA
<213> ORGANISM: Artificial Sequence
<220> FEATURE:
<223> OTHER INFORMATION: Bm-PB1-1

<400> SEQUENCE: 3
tattcgtctc agggagcgaa agcaggca                                      28

<210> SEQ ID NO 4
<211> LENGTH: 33
<212> TYPE: DNA
<213> ORGANISM: Artificial Sequence
<220> FEATURE:
<223> OTHER INFORMATION: Bm-PB1-2341R

<400> SEQUENCE: 4
atatcgtctc gtattagtag aaacaaggca ttt                                33

<210> SEQ ID NO 5
<211> LENGTH: 29
<212> TYPE: DNA
<213> ORGANISM: Artificial Sequence
<220> FEATURE:
<223> OTHER INFORMATION: Bm-NS#1

<400> SEQUENCE: 5
tattcgtctc agggagcaaa agcagggtg                                     29

<210> SEQ ID NO 6
<211> LENGTH: 34
<212> TYPE: DNA
<213> ORGANISM: Artificial Sequence
<220> FEATURE:
<223> OTHER INFORMATION: Bm-NS#2

<400> SEQUENCE: 6
atatcgtctc gtattagtag aaacaagggt gttt                               34

<210> SEQ ID NO 7
<211> LENGTH: 29
<212> TYPE: DNA
<213> ORGANISM: Artificial Sequence
<220> FEATURE:
<223> OTHER INFORMATION: Bm-M#1

<400> SEQUENCE: 7
tattcgtctc agggagcaaa agcaggtag                                     29

```
<210> SEQ ID NO 8
<211> LENGTH: 37
<212> TYPE: DNA
<213> ORGANISM: Artificial Sequence
<220> FEATURE:
<223> OTHER INFORMATION: Bm-M#2

<400> SEQUENCE: 8
atatcgtctc gtattagtag aaacaaggta gtttttt                              37

<210> SEQ ID NO 9
<211> LENGTH: 37
<212> TYPE: DNA
<213> ORGANISM: Artificial Sequence
<220> FEATURE:
<223> OTHER INFORMATION: Bm-NA1-1

<400> SEQUENCE: 9
tattcgtctc agggagcaaa agcaggagtt taacatg                              37

<210> SEQ ID NO 10
<211> LENGTH: 35
<212> TYPE: DNA
<213> ORGANISM: Artificial Sequence
<220> FEATURE:
<223> OTHER INFORMATION: Bm-NA-1413R

<400> SEQUENCE: 10
atatcgtctc gtattagtag aaacaaggag ttttt                                35

<210> SEQ ID NO 11
<211> LENGTH: 34
<212> TYPE: DNA
<213> ORGANISM: Artificial Sequence
<220> FEATURE:
<223> OTHER INFORMATION: Bm-H6-1

<400> SEQUENCE: 11
tattcgtctc agggagcaaa agcaggggaa aatg                                 34

<210> SEQ ID NO 12
<211> LENGTH: 29
<212> TYPE: DNA
<213> ORGANISM: Artificial Sequence
<220> FEATURE:
<223> OTHER INFORMATION: Ba-NP-1

<400> SEQUENCE: 12
tattggtctc agggagcgaa agcagggta                                       29

<210> SEQ ID NO 13
<211> LENGTH: 33
<212> TYPE: DNA
<213> ORGANISM: Artificial Sequence
<220> FEATURE:
<223> OTHER INFORMATION: Ba-NP1565R

<400> SEQUENCE: 13
atatggtctc gtattagtag aaacaagggt att                                  33

<210> SEQ ID NO 14
<211> LENGTH: 35
<212> TYPE: DNA
<213> ORGANISM: Artificial Sequence
<220> FEATURE:
<223> OTHER INFORMATION: Bm-PA1-1
```

-continued

```
<400> SEQUENCE: 14
tattcgtctc agggagcgaa agcaggtact gatcc                              35

<210> SEQ ID NO 15
<211> LENGTH: 36
<212> TYPE: DNA
<213> ORGANISM: Artificial Sequence
<220> FEATURE:
<223> OTHER INFORMATION: Bm-PA1-2231R

<400> SEQUENCE: 15
atatcgtctc gtattagtag aaacaaggta cttttt                             36

<210> SEQ ID NO 16
<211> LENGTH: 32
<212> TYPE: DNA
<213> ORGANISM: Artificial Sequence
<220> FEATURE:
<223> OTHER INFORMATION: Bm-PB1a-1

<400> SEQUENCE: 16
tattcgtctc agggagcgaa agcaggcaaa cc                                 32

<210> SEQ ID NO 17
<211> LENGTH: 38
<212> TYPE: DNA
<213> ORGANISM: Artificial Sequence
<220> FEATURE:
<223> OTHER INFORMATION: Ba-PB2-1

<400> SEQUENCE: 17
tattggtctc agggagcgaa agcaggtcaa ttatattc                           38

<210> SEQ ID NO 18
<211> LENGTH: 36
<212> TYPE: DNA
<213> ORGANISM: Artificial Sequence
<220> FEATURE:
<223> OTHER INFORMATION: Ba-PB2-2341R

<400> SEQUENCE: 18
atatggtctc gtattagtag aaacaaggtc gttttt                             36

<210> SEQ ID NO 19
<211> LENGTH: 12
<212> TYPE: DNA
<213> ORGANISM: Artificial Sequence
<220> FEATURE:
<223> OTHER INFORMATION: RT reaction primer

<400> SEQUENCE: 19
agcaaaagca gg                                                       12
```